United States Patent [19]

Lynn

[11] Patent Number: 5,522,804
[45] Date of Patent: Jun. 4, 1996

[54] ASPIRATION, MIXING, AND INJECTION SYRINGE

[76] Inventor: Lawrence A. Lynn, 862 Curleys Ct., Worthington, Ohio 43085

[21] Appl. No.: 231,430

[22] Filed: Apr. 22, 1994

Related U.S. Application Data

[63] Continuation-in-part of Ser. No. 196,455, Feb. 15, 1994.

[51] Int. Cl.[6] .................................................. A61M 5/00
[52] U.S. Cl. ......................... 604/191; 604/187; 604/218
[58] Field of Search .............................. 604/232, 89, 191,
604/187, 199, 204, 212, 218, 87–88, 90,
85, 415, 416, 203, 221, 219

[56] References Cited

U.S. PATENT DOCUMENTS

| | | |
|---|---|---|
| 2,737,948 | 3/1956 | Brown . |
| 3,291,151 | 12/1966 | Loken . |
| 3,494,359 | 2/1970 | Zackheim . |
| 3,511,239 | 5/1970 | Tuschhoff . |
| 3,563,240 | 2/1971 | Silver . |
| 3,680,558 | 8/1972 | Kapelowitz . |
| 3,730,170 | 5/1973 | Michael . |
| 3,807,119 | 4/1974 | Shields . |
| 3,835,835 | 9/1974 | Thompson . |
| 3,835,855 | 9/1974 | Barr, Jr. . |
| 3,976,069 | 8/1976 | Ong . |
| 3,985,122 | 10/1976 | Topham . |
| 4,051,852 | 10/1977 | Villari . |
| 4,078,565 | 3/1978 | Genese . |
| 4,437,858 | 3/1984 | Ty . |
| 4,439,184 | 3/1984 | Wheeler . |
| 4,453,934 | 6/1984 | Gahwiler . |
| 4,464,174 | 8/1984 | Ennis . |
| 4,496,344 | 1/1985 | Kamstra . |
| 4,609,371 | 9/1986 | Pizzino . |
| 4,610,666 | 9/1986 | Pizzino . |
| 4,655,747 | 4/1987 | Allen, Jr. . |
| 4,673,386 | 6/1987 | Gordon . |
| 4,693,706 | 9/1987 | Ennis, III . |
| 4,702,737 | 10/1987 | Pizzino . |
| 4,715,854 | 12/1987 | Vaillancourt . |
| 4,792,329 | 12/1988 | Schreuder . |
| 4,799,494 | 1/1989 | Wang . |
| 4,834,714 | 5/1989 | Lascar . |
| 4,838,855 | 6/1989 | Lynn . |
| 4,865,583 | 9/1989 | Tu . |
| 4,920,970 | 5/1990 | Wyatt . |
| 4,932,944 | 6/1990 | Jagger . |
| 4,941,876 | 7/1990 | Meyer . |
| 4,979,941 | 12/1990 | Ogle . |
| 4,979,942 | 12/1990 | Wolf . |

(List continued on next page.)

FOREIGN PATENT DOCUMENTS 9201485  6/1992  WIPO .

OTHER PUBLICATIONS

Silver et al, Evaluation of a New Blood–conserving Arterial Line System for Patients in Intensive Care Units, Critical Care Medicine, vol. 21, No. 4, 1993, pp. 507–511.

*Primary Examiner*—C. Fred Rosenbaum
*Assistant Examiner*—Perry E. Van Over
*Attorney, Agent, or Firm*—Cushman Darby & Cushman

[57] ABSTRACT

A drug-mixing syringe is provided that includes a barrel and a drug vial having an open distal end and sized to be slidingly received within the barrel bore. A stopper is received within and occludes the open distal end of the drug vial. The stopper includes a distal portion having at least one member projecting beyond at least a portion of the outer wall of the drug vial into engagement with an inner wall of the barrel bore when the drug vial and shopper are inserted into the barrel bore. The projecting member is displaceable relative to the barrel bore so that when the vial is inserted along the barrel bore, the projecting member is displaced along the barrel bore, and so that after the vial has been advanced to a particular extent, then retraction of the vial relative to the barrel bore causes the stopper to be displaced out of the distal end of the drug vial and retained in the barrel bore. The stopper defines at least one flow channel extending adjacent the distal portion when the stopper is received into the barrel so that when fluid flows through the barrel, fluid can flow through the flow channel.

49 Claims, 23 Drawing Sheets

U.S. PATENT DOCUMENTS

| | | |
|---|---|---|
| 4,986,278 | 1/1991 | Ravid . |
| 4,989,606 | 2/1991 | Gehrich . |
| 4,994,043 | 2/1991 | Ysebaert . |
| 5,007,903 | 4/1991 | Ellard . |
| 5,048,537 | 9/1991 | Messinger . |
| 5,078,691 | 1/1992 | Hamacher . |
| 5,102,388 | 4/1992 | Richmond . |
| 5,125,892 | 6/1992 | Drudik . |
| 5,147,323 | 9/1992 | Haber . |

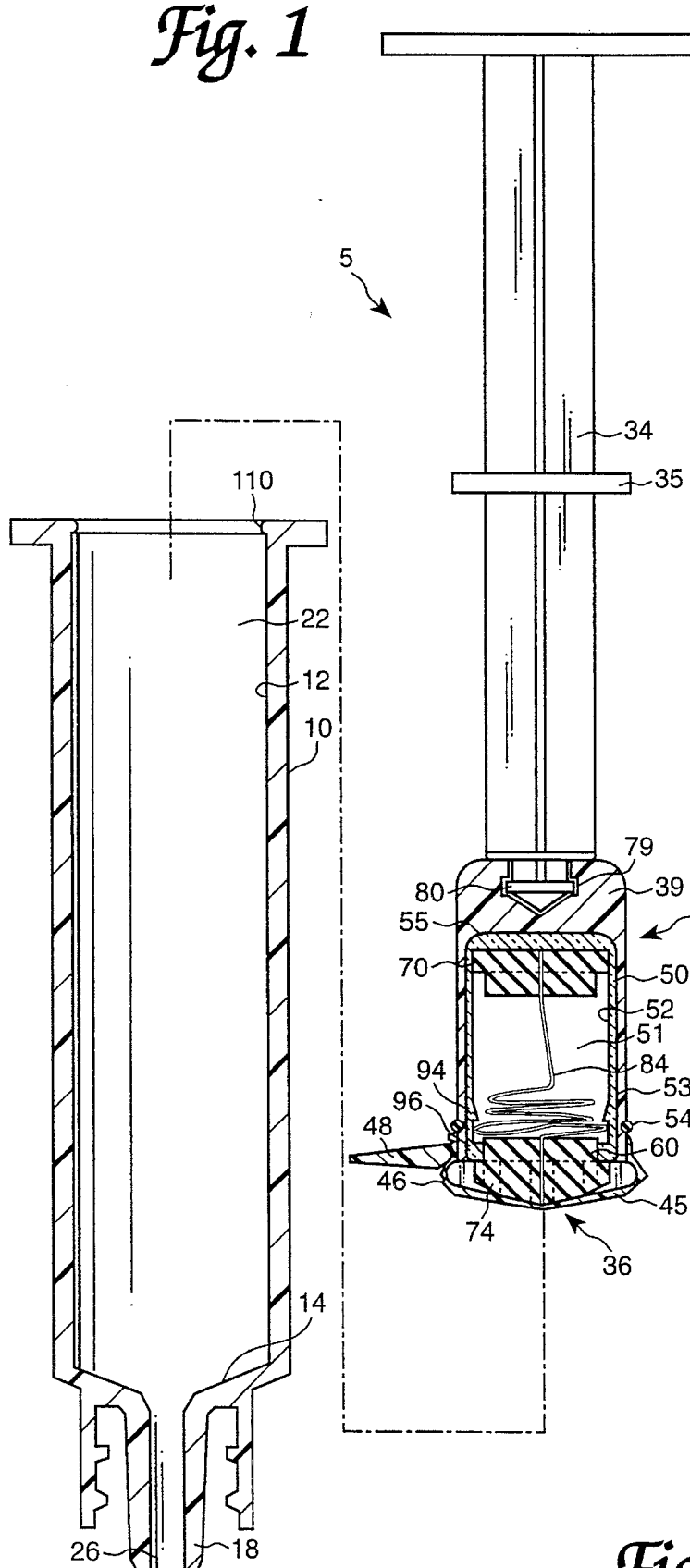
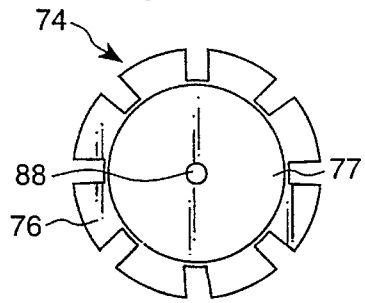
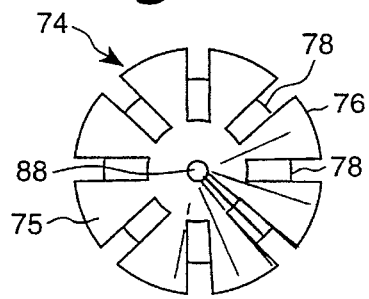
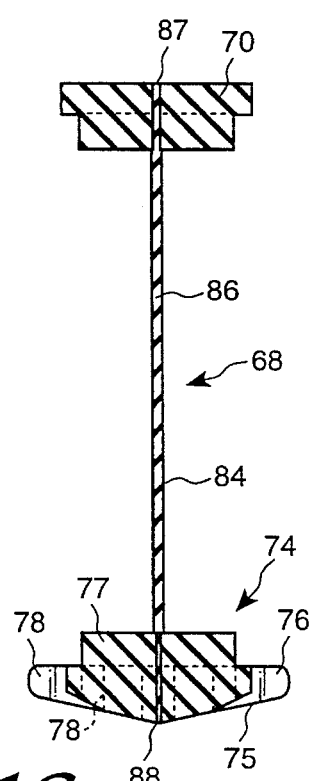

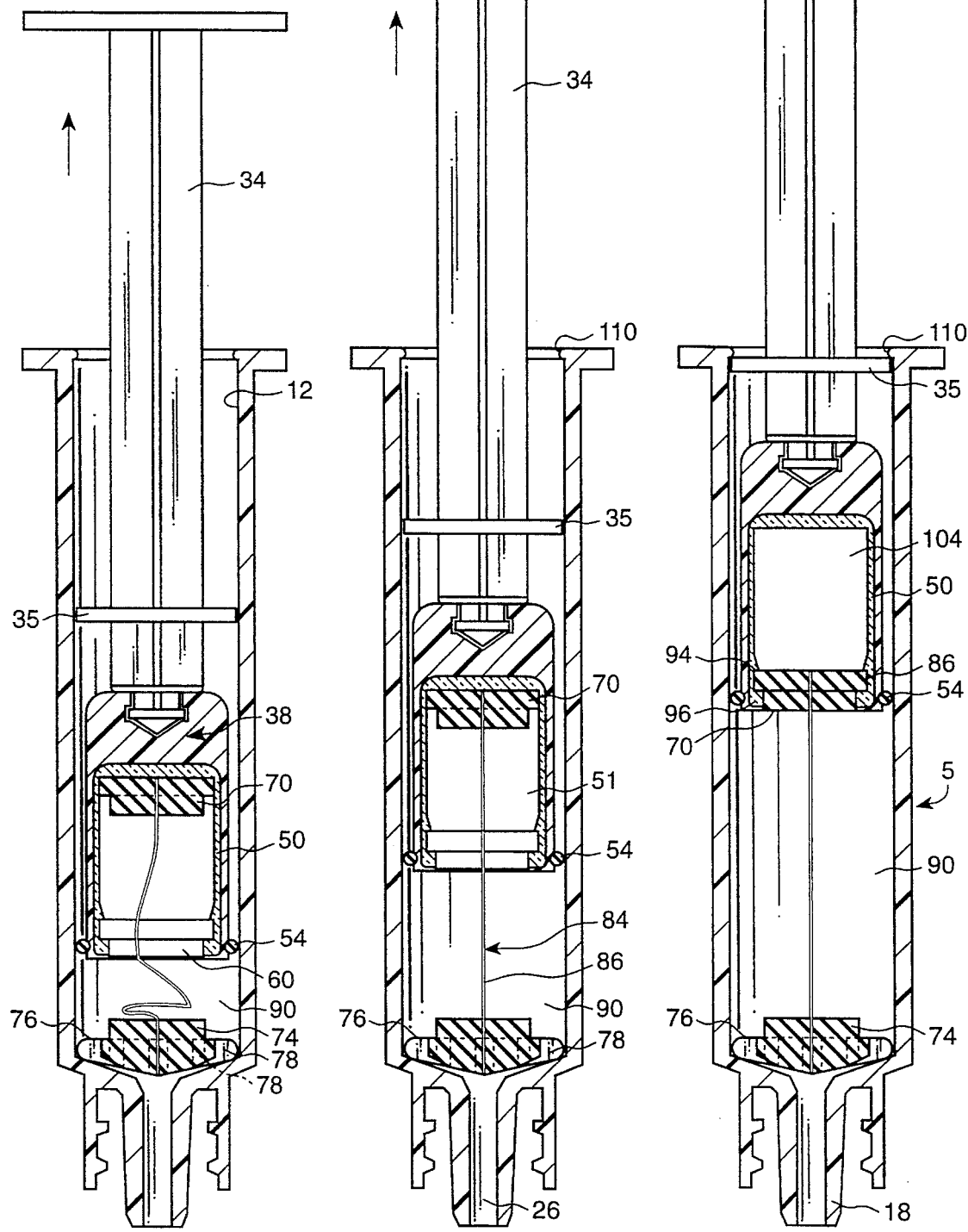

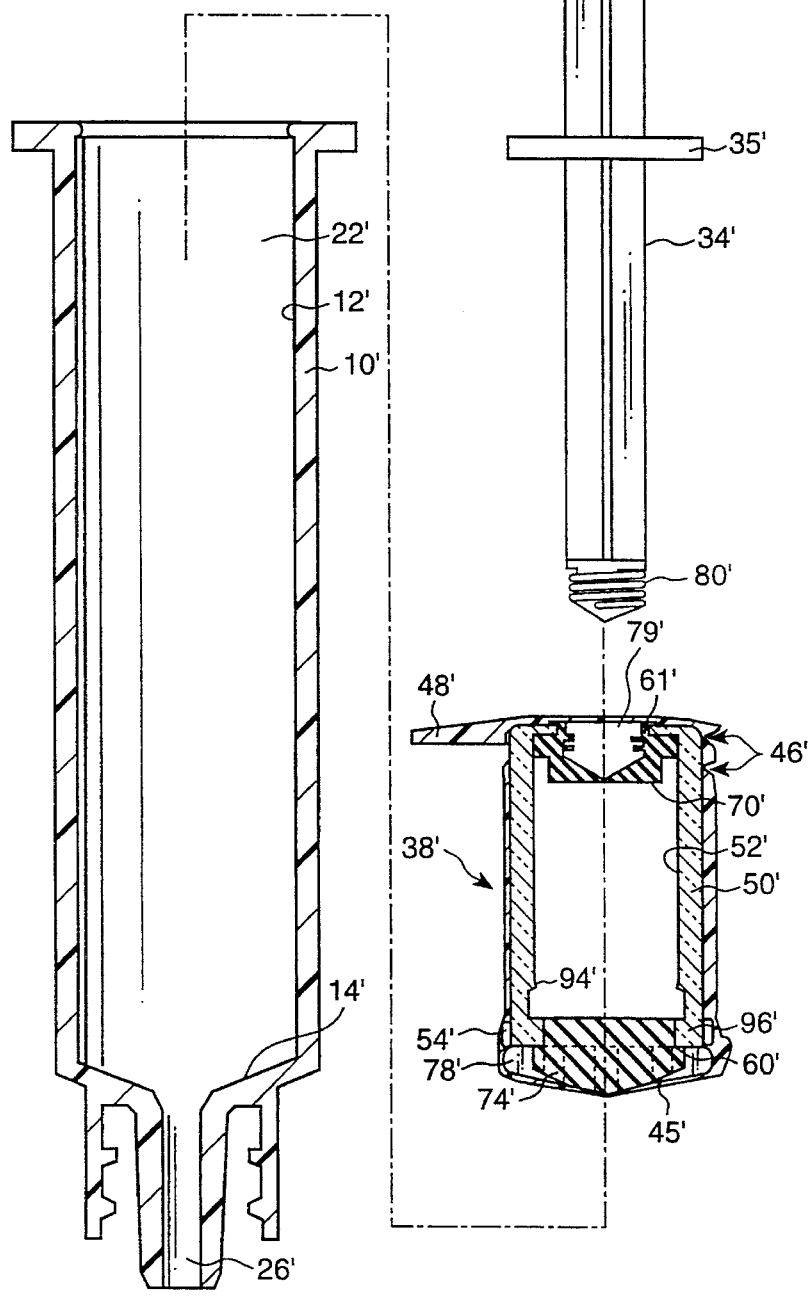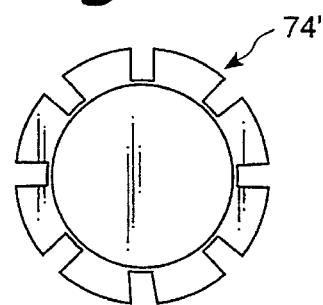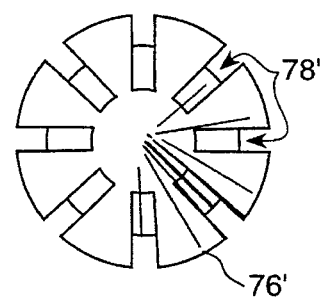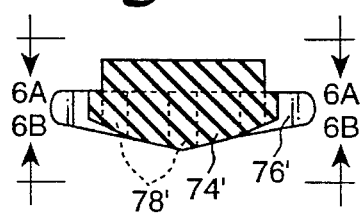

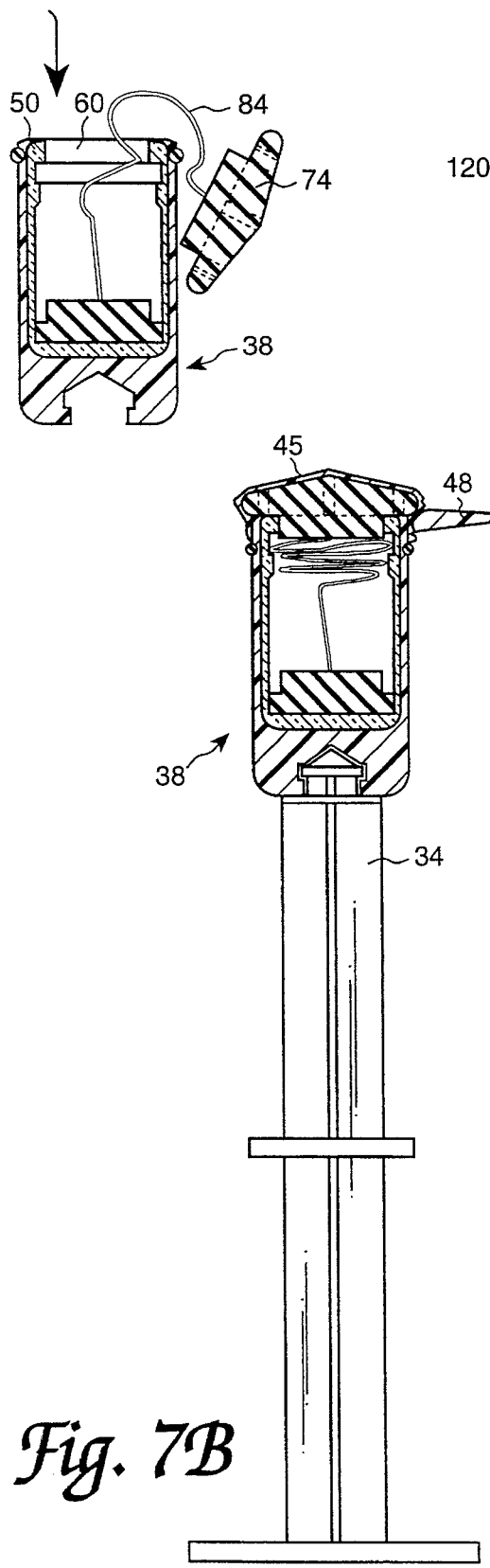
Fig. 7A
Fig. 7B
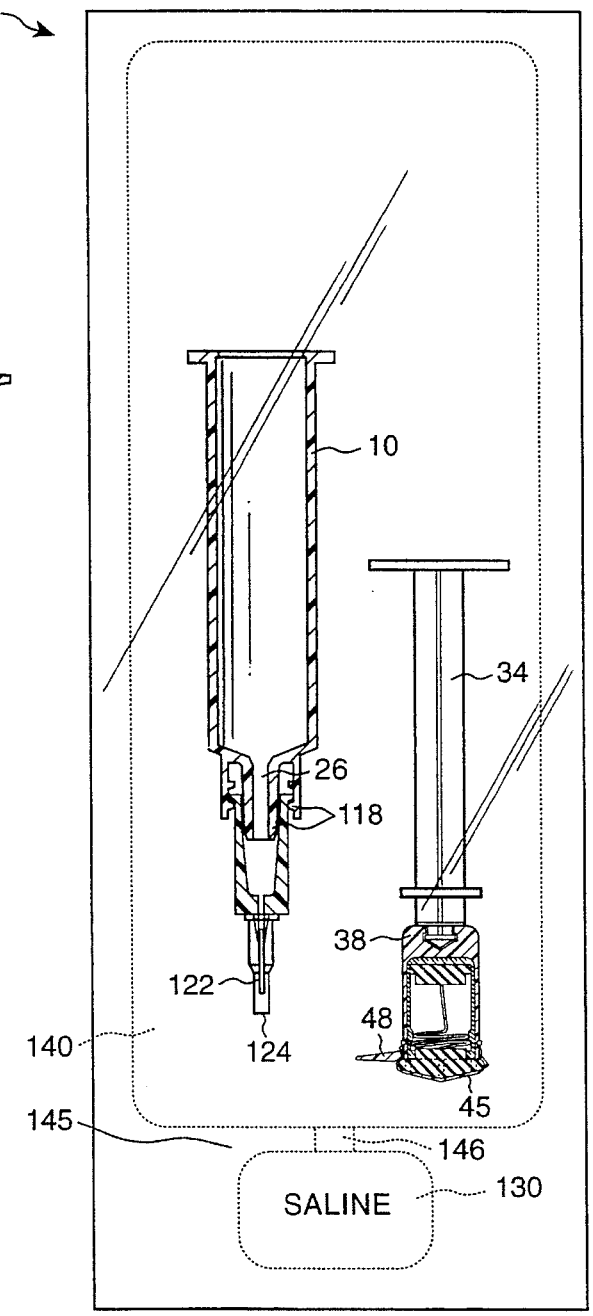
Fig. 7C

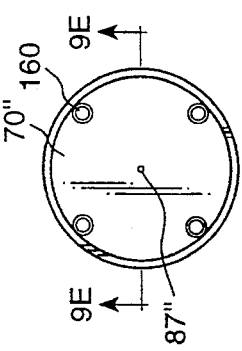
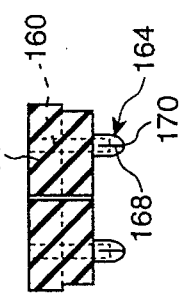
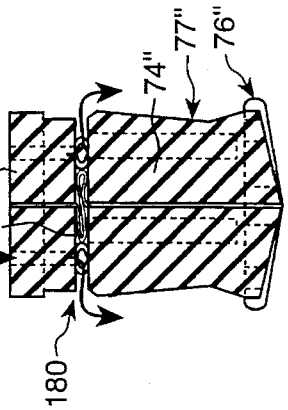
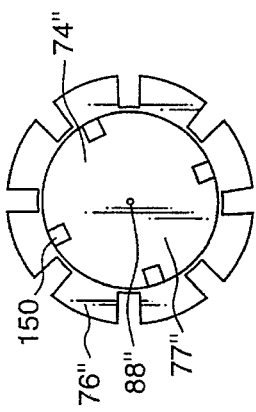
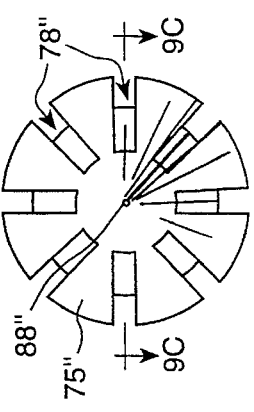
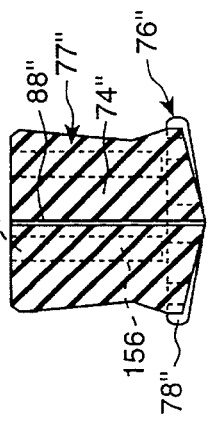
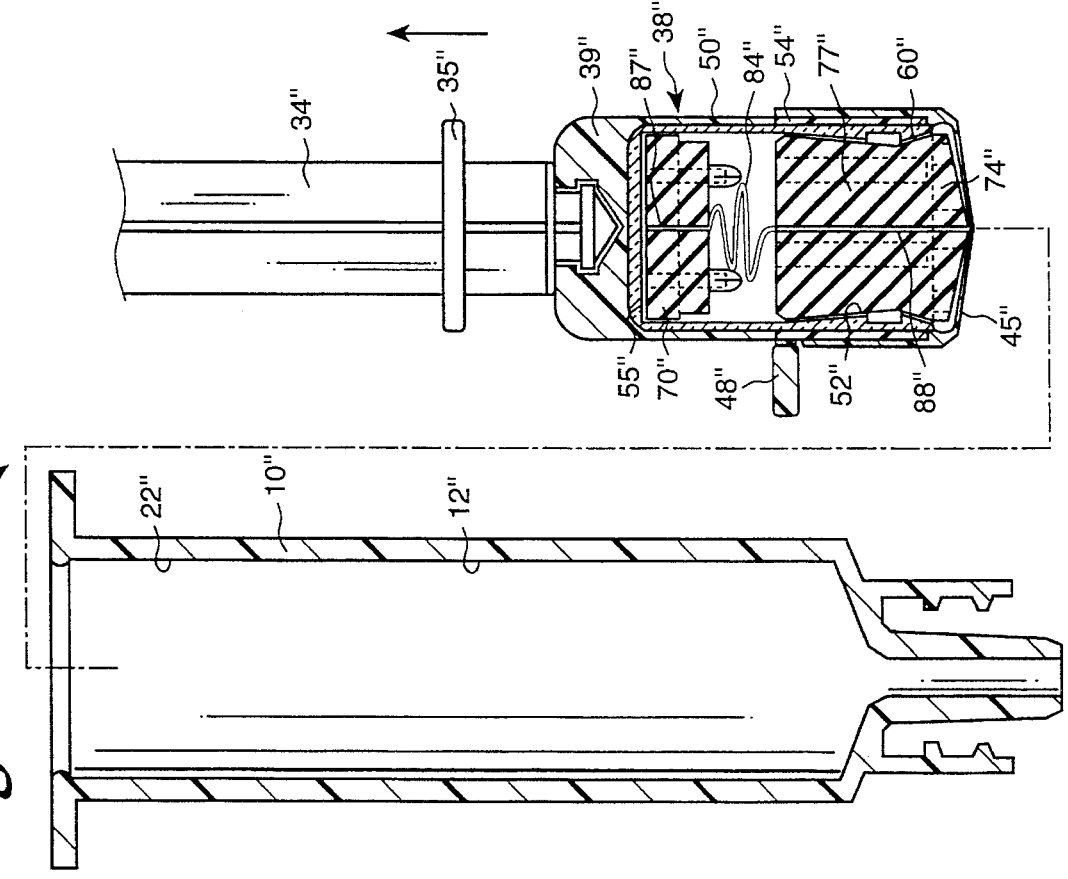

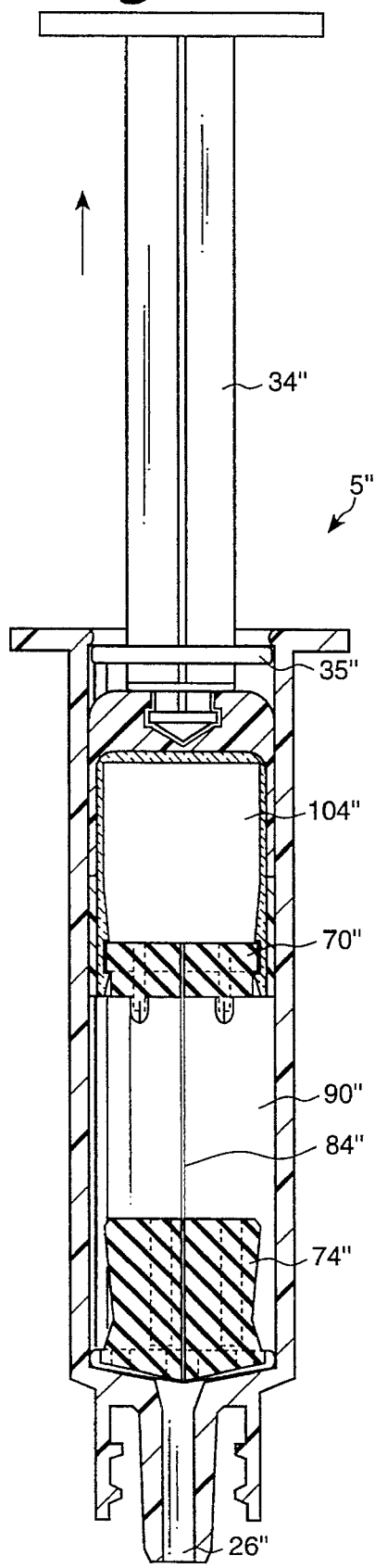
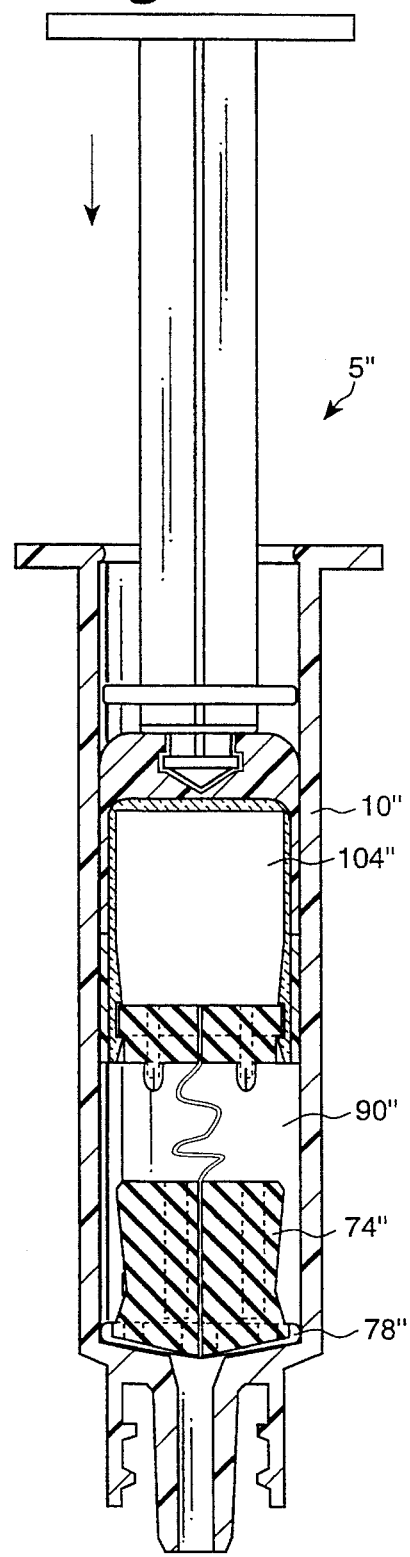
Fig. 11A
Fig. 11B

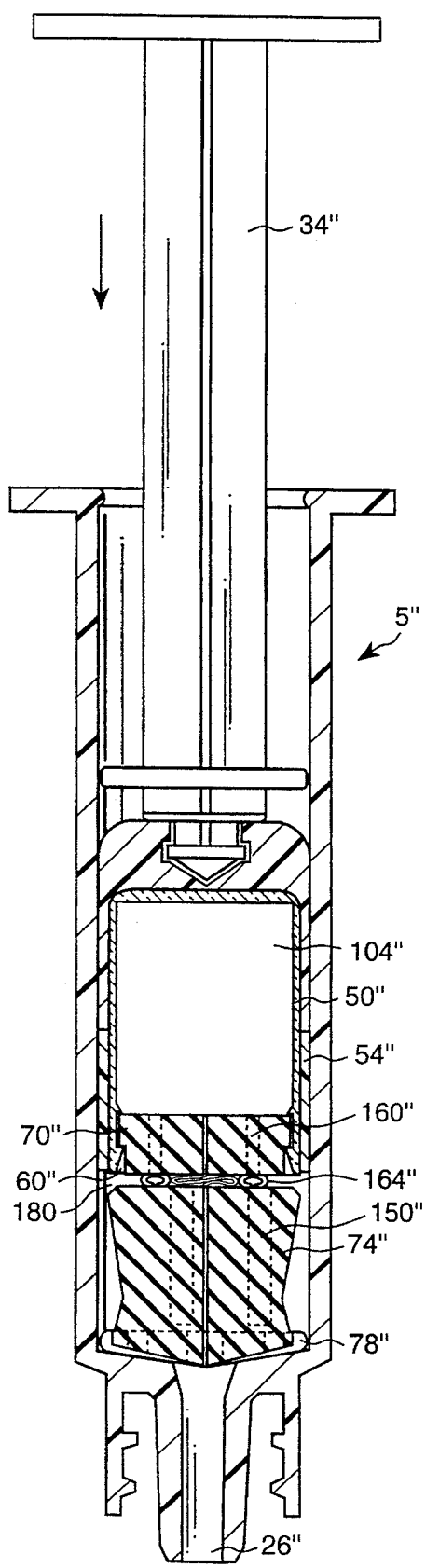
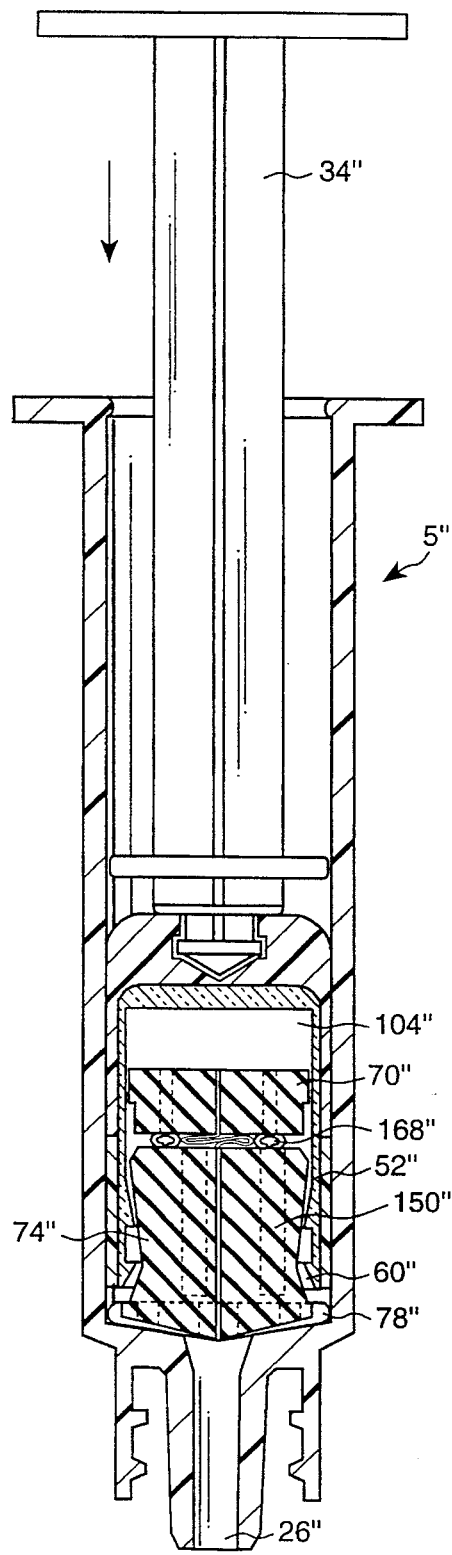

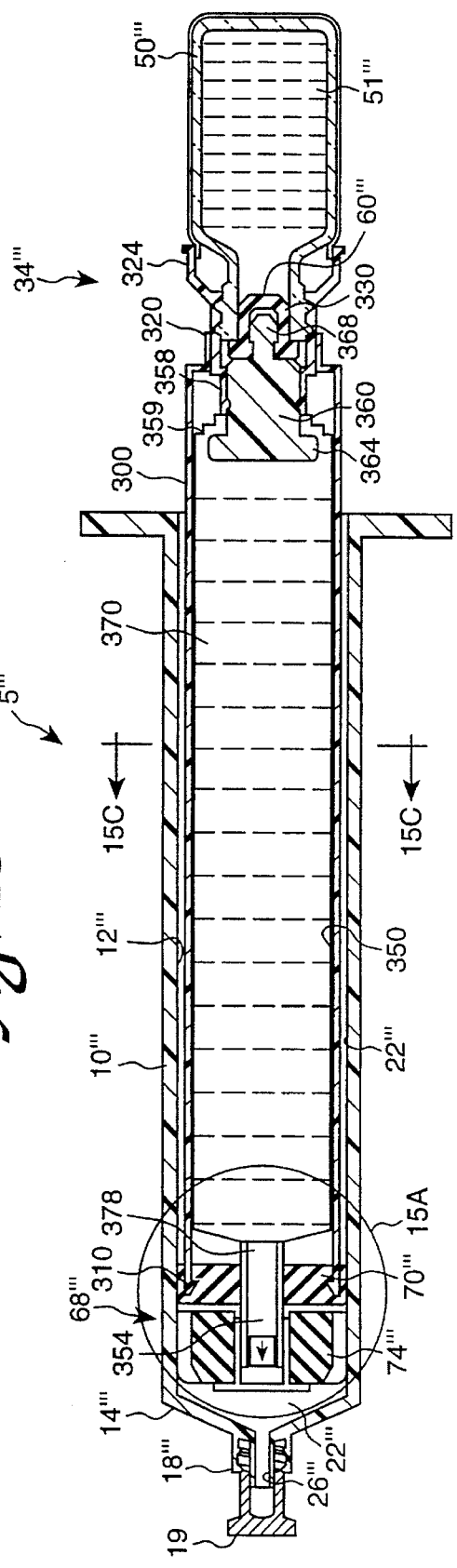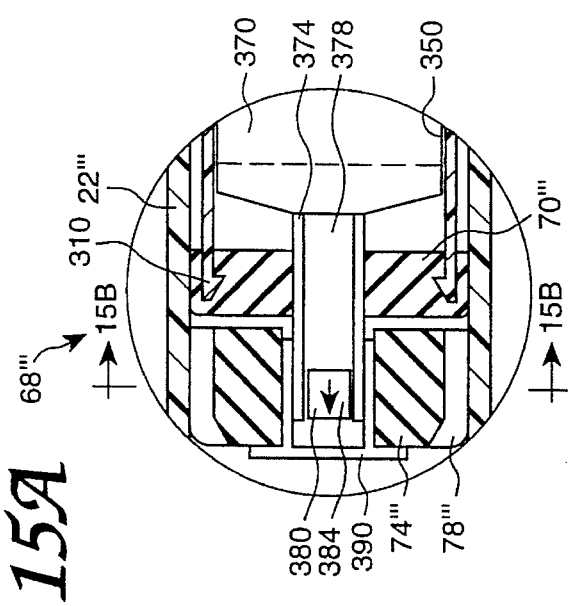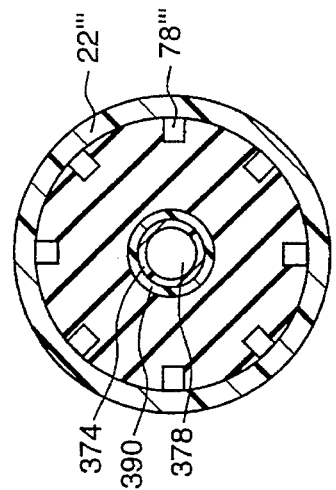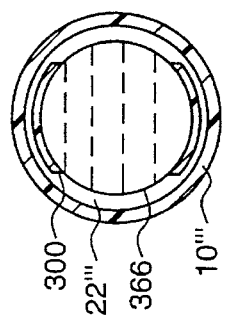

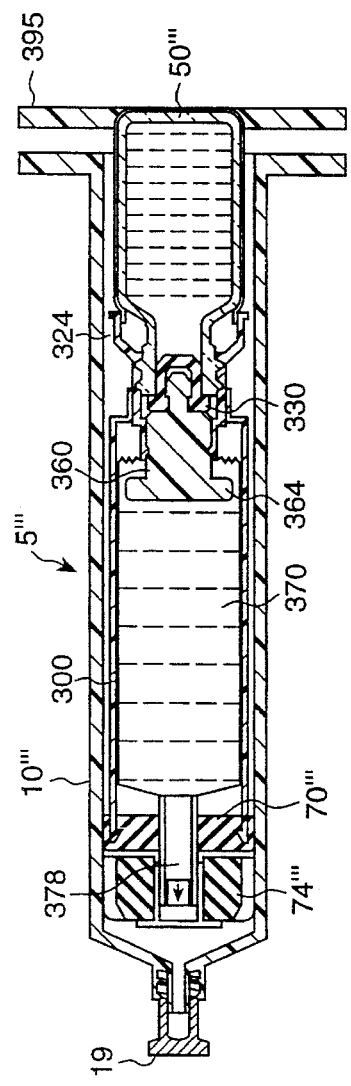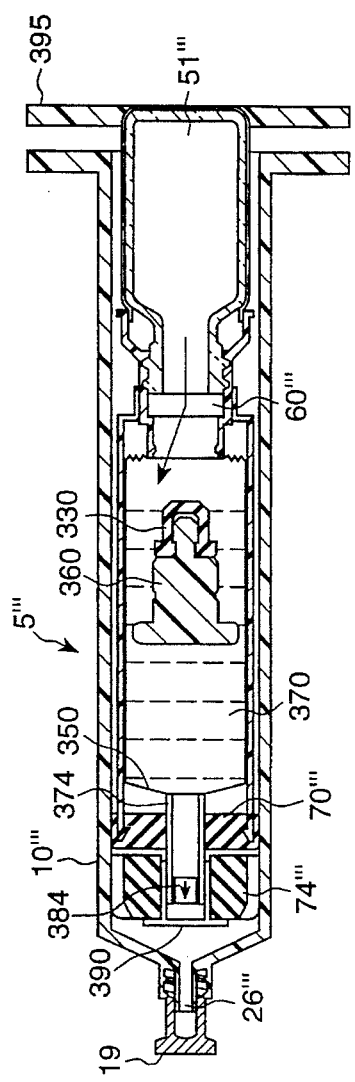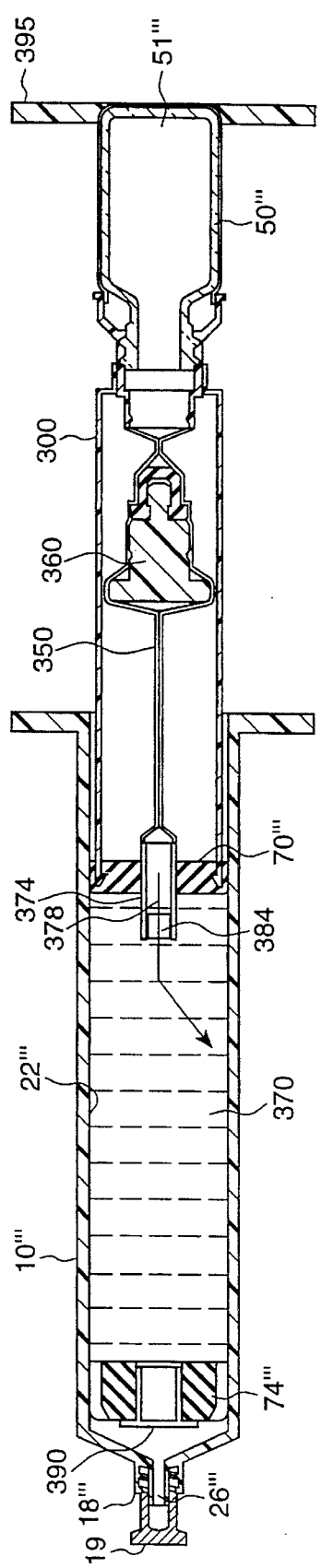

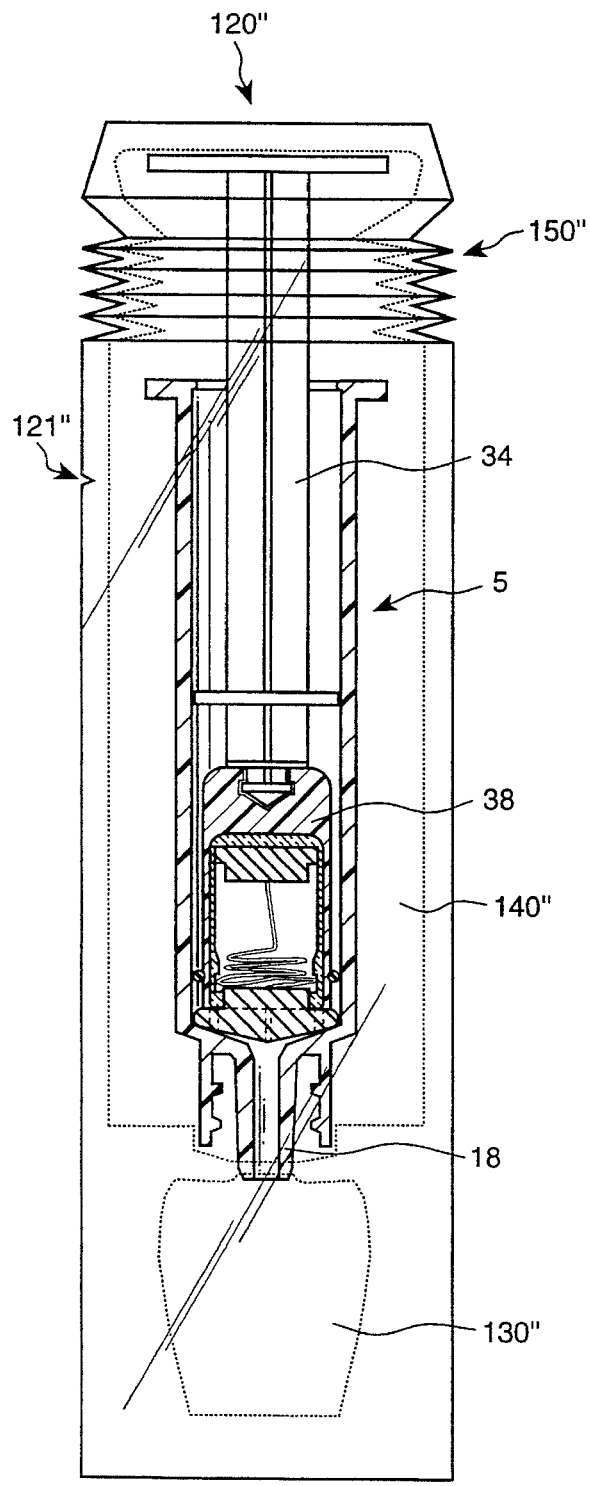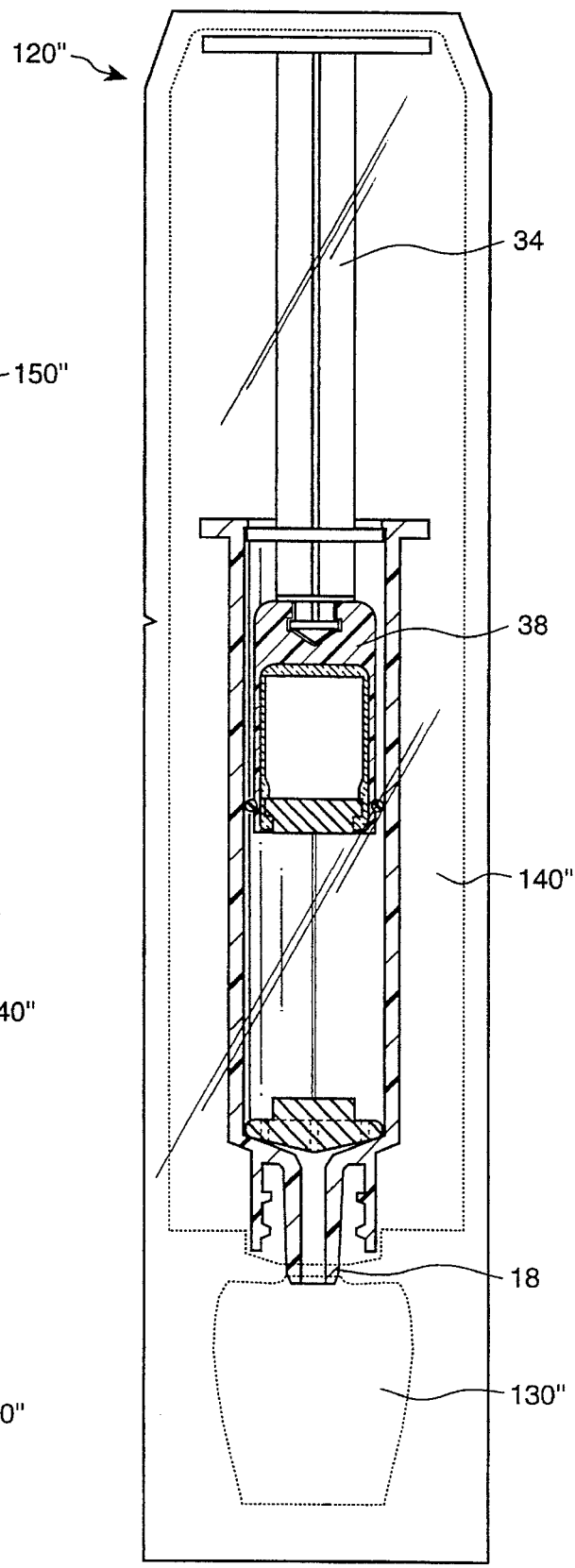

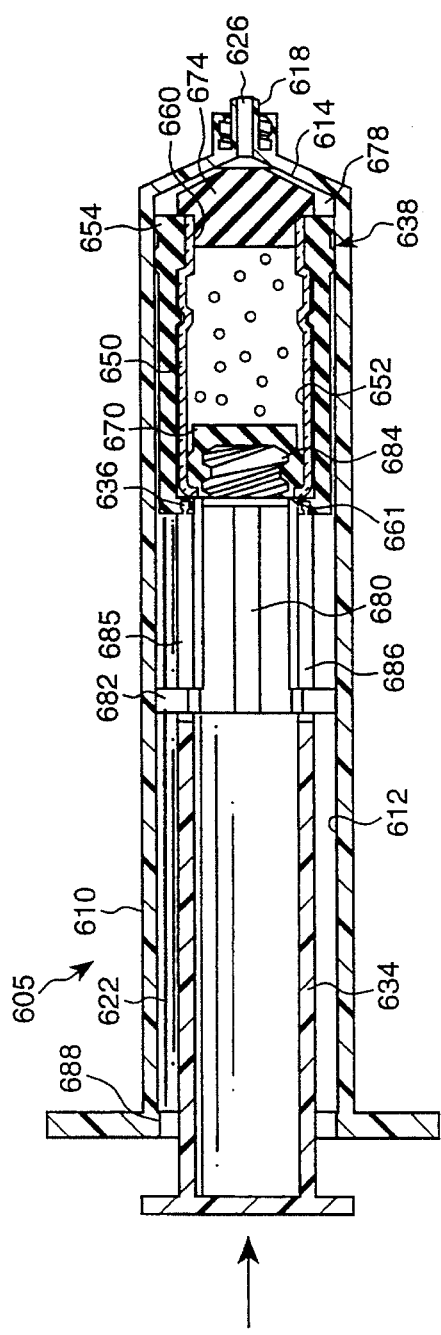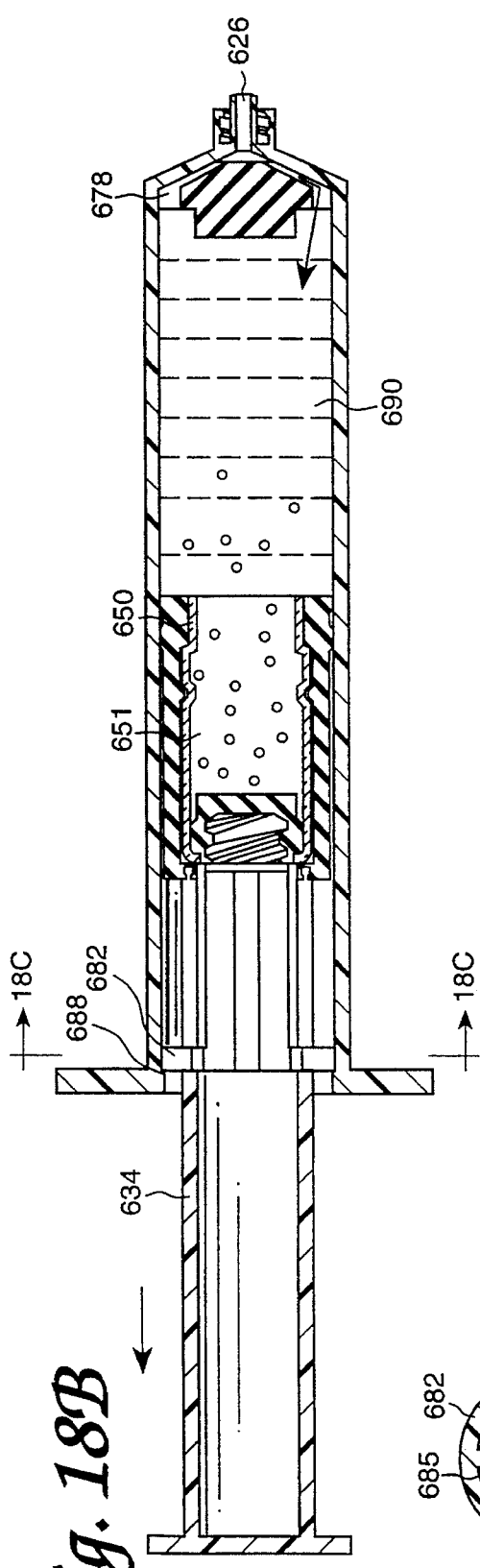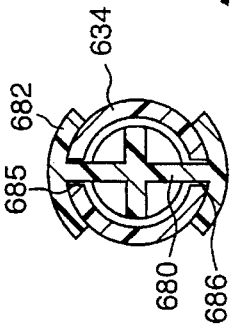
Fig. 18A
Fig. 18B
Fig. 18C

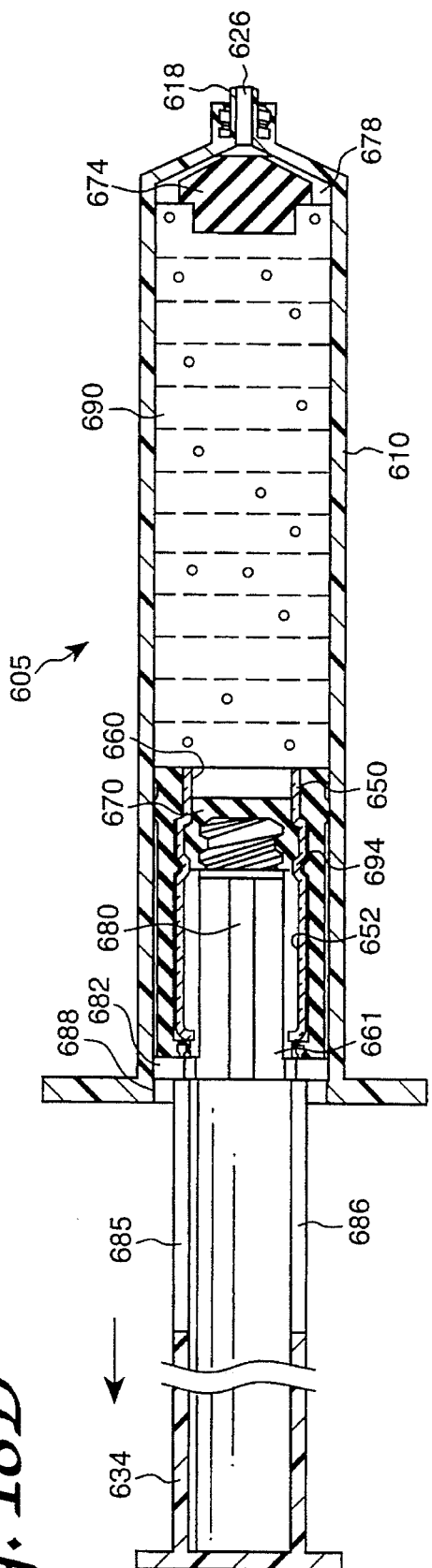
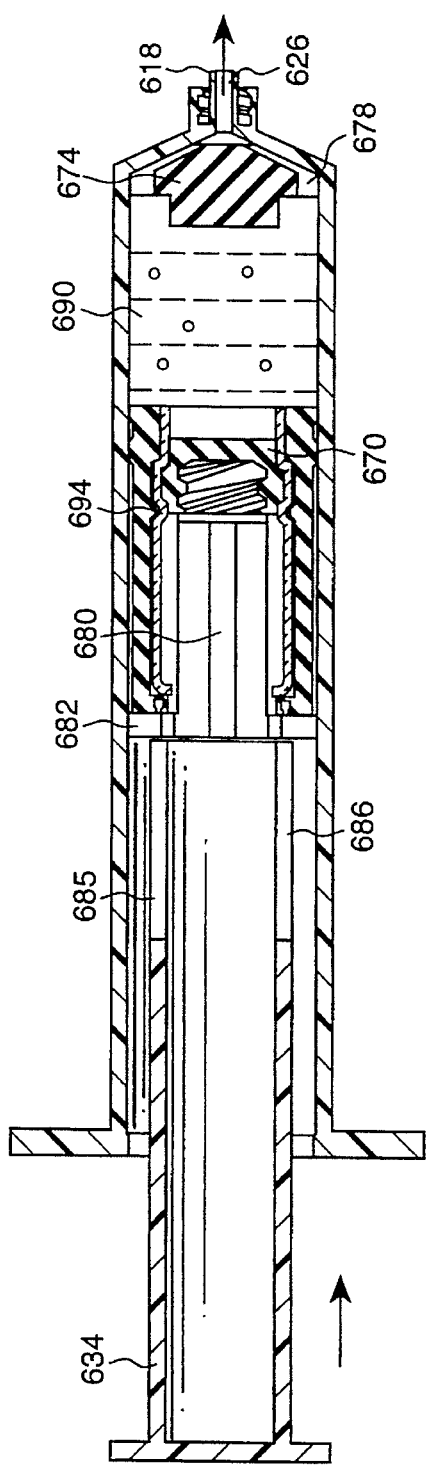
Fig. 18D
Fig. 18E

ASPIRATION, MIXING, AND INJECTION SYRINGE

This is a continuation-in-part of my co-pending U.S. patent application entitled, equential Aspiration and Injection Syringe, filed on Feb. 15, 1994 (Application #08/196,455 and having co-inventor Mark Larkin and assigned to the present inventor) (the disclosure of which is hereby incorporated by reference as if completely disclosed herein).

The aforementioned application presents the background of multi-chambered syringes which are used for sequential injection and/or the mixing of drugs and solutions. Additional background of enclosed drug-mixing systems is provided in U.S. Pat. No. 4,614,267. As described within the backgrounds of the many patents presented in the aforementioned application, it is advantageous to store a drug in a powdered or liquid form and then mix the drug in the same enclosure which is subsequently placed in fluid connection with the patient. More specifically, it is advantageous to provide mixing within a syringe so that reconstitution within a separate drug vial becomes unnecessary. This, however, must be provided at minimum cost and would preferably utilize materials to store the drug, such as glass, which have been determined appropriate by the U.S. Food and Drug Administration for long-term storage of drugs so that the evaluation of the leaching or interaction between the drug and the drug container is unnecessary. Such compatibility evaluations are associated with considerable delay and development expenses. PCT Patent Application # WO 92/01485 describes a syringe for this purpose having a glass insert and including dual pistons. The syringe, however, includes a complex barrel having multiple bores and bypass regions. This syringe requires complex molding, assembly, and sealing. However, with respect to drug administration systems, reduced cost, simplicity of design and molding, versatility of use, compatibility with automated drug dispensing systems, and ease of sterile assembly and use are the major factors defining success. It is particularly useful to provide a system using a conventional type glass vial and a convention smooth bore syringe barrel of the type in wide use and inexpensively molded of polypropylene in mass quantities and in a wide variation of bore sizes. As will be evident from the following discussion, the present invention operates to overcome many existing problems in the present art.

The sequential aspiration, mixing, and injection syringe includes a barrel having an inner wall and a main bore which is preferably conventional and smooth along substantially its entire length. The syringe includes a piston assembly having a proximal portion and a distal portion and a connecting element intermediate the portions. The portions are sized to be received into a main bore of the barrel and to fit snugly against the barrel wall. This distal portion preferably includes at least one projecting lateral member for engaging the inner walls of the barrel, thereby effectively fixing the position of the distal portion at a maximally advanced position along the barrel which preferably adjacent the distal end of the barrel, although the position could be midway along the barrel. After the pistons have been received into the barrel, the proximal portion is moveable along the barrel away from the distal portion and moveable along the barrel toward the distal portion to define a variable volume mixing chamber intermediate the proximal portion and the distal portion. The connecting element can be a fluid reservoir or a drug vial which can be comprised of glass or the connecting element can be a conduit or tube, or can be a tether or other tensile element. The glass vial can have a proximal end and a distal end. In one embodiment, both ends of the vial are open. The proximal portion can be a piston and can be positioned to occlude the proximal end and the distal portion can be a stopper to occlude the distal end of a drug vial or the distal end of a fluid reservoir or tube. The connecting element provides for mutually equivalent advancement of the proximal and distal portions along the barrel. The combined piston assembly and the connecting element can be seen to represent a reservoir or drug vial piston connectable to a syringe handle. The distal stopper is displaceable from the fluid reservoir or drug vial by retraction of the reservoir or vial away from the distal stopper and by frictional or other engagement of the distal stopper and the barrel after the reservoir or vial and the attached piston assembly have been moved to an advanced position and then the reservoir or vial is retracted from the advanced position. This allows for retraction of the proximal piston away from the distal stopper after displacement of the stopper from sealing engagement with the fluid reservoir or drug. In several embodiments, the proximal piston is further moveable along the vial toward the distal stopper. Relative advancement of the proximal piston along the vial can be caused by advancement of the handle in one embodiment wherein the proximal piston is attached to the handle. In another embodiment, wherein the proximal piston is connected to the displaced distal stopper by a tensile element, relative advancement is achieved by retraction of the vial and subsequent tensile force transmitted through the tensile element. The distal portion and the proximal portion are preferably carried by the drug vial, the distal portion being displaceable from the drug vial to open the vial into the mixing chamber, the proximal portion being moveable along the vial to displace the drug from the vial into the mixing chamber, the proximal portion effectively converting the open-ended drug vial into a closed-.ended vial piston and thereafter functioning to push the drug solution within the mixing chamber out of the syringe and into a recipient with minimal deadspace-trapped drug remaining within the syringe after injection.

A method of drug injection is provided using an embodiment having a main piston or vial piston having a handle. The vial piston includes a drug vial having a proximal end and a distal end and containing stopper piston assembly having a proximal portion connected to a distal portion by a connecting element which can be a tensile element or which can be the drug vial itself, as will be described. The syringe operates, after assembly, to achieve the following drug injection method with a single retraction and advancement of the handle, steps of: 1. aspirate diluent into the main bore; 2. open the end of a drug vial into the main bore; 3. positively expel the drug from the vial; 4. subsequently convert an open-ended drug vial into a closed-ended injection piston; 5. inject the mixed drug and diluent with minimal residual drug remaining in the syringe after injection.

As noted, the present invention can utilize a drug container or vial which can be cylindrical for insertion into a syringe barrel. The drug vial is preferably made of glass or other material which can safely contain a large variety of different drugs, either in powder or liquid form. In one embodiment, the drug vial includes a closed bottom or proximal end which may include a small air vent and an open top or distal end which is preferably widely open and can, therefore, easily be filled by conventional automated drug dispensing systems. The drug vial can include a narrow neck and larger body to facilitate handling by automated equipment. The drug vial further preferably includes an outer housing member which can be polymeric. At least one sliding member is preferably provided about the vial to slidably engage the syringe barrel bore to facilitate advancement and retraction of the drug vial along the syringe barrel bore. The sliding member can be a thin rubber boot or sleeve. Alternatively, the polymeric housing member may itself be sized to sealingly engage the bore. The sliding member can be a rubber wiper of the type utilized in conventional syringe pistons or can be an o-ring or soft polymeric ring or otherwise fashioned. The sliding member is preferably carried by the housing or vial and may be positioned proximal, distal to, or along the length of the housing or vial. The outer member further can have a recess for receiving the retainer of the handle of a conventional syringe piston or, alternatively, the handle can be molded integrally with the outer vial housing member. The vial can, therefore, be connected to or contained within the handle or can be integral with a handle. In an embodiment, the vial and handle are made of glass and are integral and molded together, thereby eliminating the need for the outer polymeric housing member. In one embodiment, the vial piston includes a piston stopper assembly with a proximal stopper portion for positioning adjacent the closed end of the drug vial and a distal stopper piston portion for occluding the open end of the drug vial. Both portions can be comprised of conventional material utilized for rubber stoppers in drug vials so that contact with the drug and the rubber stopper piston assembly is provided, as is conventional, thereby eliminating the potential for material-related incompatibility. The proximal and distal portions are connected or linked by the drug vial and can be carried by the drug vial. In one embodiment, the portions are further preferably connected by a tether or by bands or other tensile connecting elements which can be comprised of conventional material used in the construction of rubber stopper pistons so as again to allow direct contact with the drug within the glass container without the need for further study to determine compatibility. The two stopper pistons can be molded as a single pan with the connecting rubber tether. In one embodiment, a vent is provided for providing vent connection between the proximal face or end of the proximal piston and the atmosphere or between the proximal face of the proximal piston and the distal face or end of the distal stopper. In one preferred embodiment, the vent passes through the tether, the tether comprising a hollow tube having a bore and extending to connect bores through the proximal piston and the distal stopper. This defines a flexible tether vent which operates to limit retraction movement of the proximal piston, thereby to cause advancement of the proximal piston relative to the retracting drug vial and further to vent fluid or air into the drug vial intermediate the proximal piston and the closed end to permit advancement and to allow enlargement of an otherwise sealed nascent proximal compartment within the vial and to fill the enlarging proximal compartment with fluid. In another embodiment, the vent passes through a small opening in the otherwise closed bottom of the drug vial, the vent being occluded by the proximal piston prior to use. The vent can pass into a large volume space within a hollow handle to provide a sealed source of sterile vented atmosphere or liquid with a minimal induction of negative pressure. The width of the outer wiper may be varied so as to allow use of the same housing and vial within syringes of variable diameter and volume. This allows modification of only the wiper when different volumes of diluent are intended for use with, for example, a powdered drug so that a wide variety of variable sized vials and housings need not be constructed for syringes having bores of variable diameters.

In the manufacture of one preferred embodiment having a drug vial with a closed bottom, the proximal piston is inserted into the glass vial and this can be performed, for example, by radial compression of the proximal piston and insertion such that the proximal piston is fully advanced against the closed bottom of the glass vial. The tether or bands are preferably of adequate length to extend out through the open top of the glass vial such that the top or distal stopper does not, at this time, occlude the opening in the top of the drug vial so that powdered or liquid drug may easily be inserted at this time into the drug vial as by automated drug dispensing systems. Once an adequate volume of powdered or liquid drug has been inserted into the drug vial, the distal stopper with its associated residual tether is inserted into the top of the drug vial to occlude the opening in the drug vial. The stopper may have a laterally projecting rim and a main stopper portion which can be received by a compression fit, as is known in the art, into the glass opening to seal the opening. A distal sealing vial cover may then be provided to sealingly retain the cap and drug within the vial for long-term storage. After the vial cover has been removed, the distal stopper may be displaced from the glass opening by longitudinal force directed against the rim, away from the opening of the vial.

The distal vial stopper preferably includes flow channels. The flow channels preferably do not provide communication of the vial chamber with the atmosphere when the stopper is within the vial The flow channels can be slots along the outer laterally projecting rim or perimeter of the stopper or can otherwise be through the stopper piston. The flow channels may be defined by the inner barrel wall and the distal stopper. The channels can be longitudinally slit valves or other valves which are tightly closed at rest, but which are opened by contact with the distal end of the syringe. The laterally projecting portion of the distal stopper preferably has a diameter exceeding the diameter of the syringe bore so that the distal stopper is radially compressed by the barrel and is tightly fit within the barrel by elastic compression against the barrel wall. This allows for reliable fixation of the distal stopper within the barrel at the maximum point of advancement into the barrel, which can be adjacent the distal end of the main barrel bore. This allows the vial to be reliably and easily opened within the barrel by single handle retraction. Since the distal stopper will be fixed by tight elastic compression and frictional engagement with the wall, longitudinal retraction force on the vial will displace the vial away from the distal stopper.

In this way, each drug vial may be sized to be received into conventional automated drug dispensing equipment and can be covered and maintained for long-term storage within a conventional securely sealed polymeric enclosure. The vial can then be connected with the handle and can be packaged in a flexible sterile container along with the barrel, cannula, cannula cover, and even the diluent material in a single flexible sterile packaging enclosure for shipment and storage. The components can be completely assembled within the closed or partially closed sterile package immediately prior to use. This allows for easy packaging and storage and assures sterile assembly, which is otherwise difficult to reliably achieve when loading a piston into a syringe barrel in an open environment.

As noted, in a preferred embodiment, the handle with its vial piston is packaged with a separate syringe barrel within a single sterile flexible enclosure and constructed so that the vial piston may be unsealed and loaded into the barrel within the same sterile package which was used for storage. To prepare the vial for activation, the pharmacist can grasp a projecting tear tab on the sealing vial cover through the flexible package and remove the cover from the vial stopper, thereby exposing the enclosed distal stopper. The vial piston is then inserted into the syringe barrel by contacting the outside of the barrel through the package and inserting the distal end of the vial piston into the barrel. The vial piston is then fully advanced until the distal stopper contacts the distal end. The cannula can then be inserted into a liquid-filled compartment or container within the sterile enclosure. The vial piston can then be retracted. The syringe will then be filled by aspirating liquid enclosed within the enclosure into the barrel. The filled and mixed syringe can then be sent to the floor or to the patient's home for use, or can be frozen for long-term storage, still within the unopened and sealed original sterile enclosure.

In operation for injection, the handle is advanced until the distal stopper piston reaches a venting position along the barrel, if the handle had not previously been advanced to that position during assembly. The location of the venting position depends on the position of the source of diluent. In the preferred embodiment, the venting position is adjacent the distal end of the barrel. However, if the diluent is positioned within the syringe, the venting position can be, for example, midway along the barrel. The handle is then retracted, pulling the drag vial away from the distal stopper which includes a member or portion which is tightly retained against a portion of the barrel. This causes opening of the drag vial, thereby allowing fluid to flow into the drug vial and the drag to mix with fluid. In the preferred embodiment, the diluent fluid is stored external the syringe and the venting position is adjacent the distal end of the syringe barrel, leaving the distal stopper retained adjacent the distal end upon retraction of the vial. The distal stopper is preferably retained by tight frictional engagement with the smooth barrel or can be retained by detents along the barrel. In embodiments utilizing a tensile element, as the handle is further retracted, the tensile element will become extended, thereby transmitting tensile force to the proximal piston so that further retraction of the handle and the attached vial will cause the proximal piston to be advanced relative to the retracting drug vial so that substantially all drug and solution within the vial is pushed distally by the advancing proximal piston into the main bore or mixing chamber of the syringe. The vent preferably provides fluid communication between the vial intermediate the proximal piston and the closed vial end, thereby relieving any negative pressure within the newly enlarging closed proximal vial chamber by the passage of fluid or air through the vent into the vial proximal the proximal piston. After retraction, the solution in the mixing chamber can be agitated. If preferred, an amount of air can be initially provided during manufacture within the vial to facilitate agitation. Once the handle has been fully retracted, the proximal piston is received and retained within the distal end of the drug vial, thereby occluding the distal end of the drug vial so that the drug vial itself with its now distally occluding stopper piston now can function as a closed injection piston with the fully advanced proximal piston as its distal face. The vial can be advanced to cause injection of the mixed drug and solution into the patient with minimal residual remaining in the syringe. In one preferred embodiment, the diluent stored within the enlarging proximal chamber is later used to provide subsequent flushing of the syringe and can provide flushing of the injected drug from the deadspace of the recipient tubing. Utilizing this embodiment, during injection, once the vial piston has been fully advanced against the distal stopper, the proximal stopper is displaced from the end of the drug vial and the fluid which had been received through the vent and stored within the vial proximal the proximal piston is now displaced by the forced movement of the proximal piston back toward the closed end of the drug vial. Flow channels provided within the proximal piston allow displacement and flow of fluid from the drug vial chamber into the now virtually absent mixing chamber and out the distal conduit to flush the syringe, the conduit, and the deadspace of the tubing which is connected to the conduit and which has previously received the drug solution mixture from the conduit. This embodiment, therefore, provides for: 1) enclosed sterile insertion of a handle and piston assembly containing a powdered or liquid drug into a syringe barrel; 2) enclosed wide opening of the drug vial within the syringe barrel; 3) aspiration of diluent into free contact with the now exposed drugs from within the vial and for positive expulsion of all drug from within the vial; 4) aspiration of diluent which can later serve as a flush solution into an enlarging proximal chamber within the drug vial; 5) injection of the mixed drug solution through or around the displaced stopper into the recipient; 6) injection of the flush solution through the distal portion of the syringe and out the distal conduit to flush the syringe, the distal conduit, and at least a portion of the recipient tubing free of drug solution. It can be seen, therefore, that whether a tensile element is utilized or whether the piston handle is connected to the proximal piston, advancement of the proximal piston can be achieved for positive expulsion of the drug and, at the same time, an enlarging proximal chamber is formed within the vial which can receive fluids which can subsequently be displaced back through the distal portion of the syringe to flush the syringe.

In one embodiment, the diluent is contained within the distal portion of the syringe for mixing within the drug vial. In another embodiment, the distal conduit end of the syringe can be connected to a flexible bag containing a specific volume of diluent for aspiration into the syringe which can be stored within or can be a compartment of the main enclosing flexible package for enclosed aspiration. The conduit can be placed in fluid connection with a fluid source through a cannula connected to the distal end of the syringe. Alternatively, the fluid source may be sealingly engaged to the syringe during manufacture and then enclosed in a main flexible package. Further, alternatively, a compartment of the main flexible package containing the diluent can be sealed about the distal end of the syringe to minimize the amount of packaging required while further eliminating exposure during aspiration. A third embodiment utilizes a system wherein the syringe tip is inserted into a receiver having a one-way valve and connected to a multi-dose large volume reservoir of diluent in a hospital pharmacy of I.V. mixing area. When drug mixing is desired, the tip is inserted into the receiver and a specific volume of diluent is aspirated. The maximum aspirated volume can be preset by stops or by the length of the tether. The one-way valve prevents any potential for reflux of mixed drug solution into the reservoir.

In another preferred embodiment, the stopper assembly is provided including a connecting element intermediate the proximal piston and the distal stopper. Like the previous embodiments, the embodiment preferably includes an inner wall defining a main bore and extending to a distal tip and a conduit extending through the distal tip. The distal stopper includes projecting lateral walls for engaging. A seal is preferably provided occluding the conduit adjacent the distal tip. A diluent reservoir is further provided proximal the proximal piston and is preferably contained within the handle of the syringe. The diluent reservoir is preferably a flexible bag of fluid and is comprised of conventional material for making flexible intravenous bags of fluids, such as PVC. A flow passage way which can be a tubular extension of the PVC reservoir, is preferably provided through the proximal piston. The flow passage way is occluded by the distal stopper or can preferably be occluded by a cap which can be extracted from its occluding position along the flow passage way by the distal stopper. In the preferred embodiment, the distal stopper is integral with or is otherwise joined with the cap. The distal stopper preferably includes at least one membrane such as projecting lateral walls engaging as by tight frictional contact the inner wall or walls of the barrel, thereby effectively fixing the position of the distal stopper piston at a maximally advanced position along the barrel which is preferably adjacent the distal end of the barrel, although the position could be midway along the barrel. The flexible fluid reservoir can contain the first pharmaceutical component, which is preferably diluent or liquid drug. A second pharmaceutical component can be contained within the proximal portion of the barrel distal to the maximum advancing position of the distal stopper or can be within a drug vial connectable to a drug vial connector carried by the proximal end of the reservoir. The proximal end of the reservoir can include a reversibly sealed opening for transferring fluid from the reservoir into the drug vial and for transferring mixed drug and fluid out of the drug vial into the reservoir. In operation, the handle which has been advanced to a fully advanced position, is retracted. During retraction of the handle, the handle with its retained reservoir and proximal piston are pulled away from the distal stopper, thereby opening the distal end of the reservoir into the barrel of the syringe. Continued retraction of the handle results in negative pressure developing within the distal end of the syringe, thereby withdrawing fluid from the open end of the reservoir into the barrel. As the fluid is withdrawn, the flexible container collapses until all of the fluid is withdrawn into the barrel, at which time further retraction cannot be accomplished due to the development of a vacuum within the container. Furthermore, a detent can be provided which prevents further retraction to assure that excessive vacuum does not develop within the syringe. The flexible package dynamically collapses, thereby producing a collapsing valve mechanism preventing substantial transmission of negative pressure from the distal end of the syringe to the drug vial; although, such transmission of negative pressure would not have significant adverse consequences with the preferred embodiment in any regard. At this time, all of the mixed fluid and diluent have been displaced into a nascent mixing chamber intermediate the distal stopper and the proximal piston and subsequently this fluid can be injected by advancing the proximal piston, thereby pushing the fluid through the flow channels and the distal stopper and out the distal end of the syringe after the seal has been removed from the distal end of the syringe. A one-way valve can be provided in the flow channel through the proximal piston to prevent reflux or displacement of fluids from the mixing chamber back into the flexible reservoir during injection.

It is the purpose of the present invention to provide a drug injector which can provide long-term storage of powdered or liquid drug and subsequently allow enclosed mixing of this powdered or liquid drug with a diluent within the injector through a large opening to assure complete and easy mixing. It is the purpose of this invention to provide a distal vial stopper which can seal a reservoir or drug vial during storage, but which can provide a flow of fluid through or about the stopper once the reservoir or vial has been inserted into a syringe barrel and once the stopper has been displaced from the vial. It is further the purpose of this invention to provide a drug positioned between a piston stopper assembly connected by a tensile element within a vial so that the drug can be pushed out of the vial into a mixing area by traction on the tensile element. It is further the purpose of this invention to provide a closed drug vial which can be selectively widely opened within a closed container to allow free mixing of the drug contained within the vial with a diluent. It is further the purpose of this invention to provide a drug vial and piston stopper assembly wherein the drug vial first has a closed end containing, the drug and wherein the end can be opened so that the drug can mix with a diluent and wherein the end can again be subsequently closed so that the drug vial can function as a deadspace-free piston for injecting the mixed drug solution into the patient. It is further the purpose of the invention to provide a syringe handle containing a drug vial and defining a drug vial piston within the syringe. It is further the purpose of this invention to provide a multi-compartment injection system having a syringe barrel and a piston and including a glass drug vial compartment for long-term storage of a drug, and a second compartment for storage of a specific volume of diluent and wherein the second compartment is sealed and can be positioned inside or outside the syringe so that solution may be displaced into the vial to mix with the drug by retraction of the piston along the barrel and simultaneous unsealing of the vial or the diluent compartment. It is further the purpose of this invention to provide a drug storage, mixing, and injection apparatus which allows long-term storage of a drug within a glass vial comprehensively enclosed mixture within a syringe and then complete positive expulsion of all of the contained drug into a mixing chamber within the syringe. It is further the purpose of this invention to provide a system which allows positive displacement of diluent into a syringe compartment containing powdered drug within an open-mouthed glass vial and subsequent injection of the diluent mixed with the drug utilizing closure and subsequent advancement of the glass vial within the syringe. It is further the purpose of this invention to provide a system and method for the enclosed sterile assembly of a drug mixing syringe and to provide a system for enclosed aspiration of fluid into the syringe for mixing with the drug within a single inexpensive sterile flexible enclosure. It is further the purpose of the invention to provide a syringe which can sequentially aspirate a diluent and flush solution into two separate compartments, provide for drug mixing with the diluent, and then provide sequential injection of the drug solution followed by the flush solution to flush substantially all drug from the syringe and to flush the injection site free of drug solution. For some purposes, it is preferable to provide the diluent in a manner such that the diluent is packaged within a syringe component wherein the drug vial can be packaged external to the syringe and where free and complete mixing between the drug vial and the diluent can be performed within a syringe component. In one feature of the invention, the connection of a sealing capping member of the diluent reservoir to a cap extraction member can fixedly engage a portion of the syringe barrel so that the cap can be extracted from the diluent reservoir by retraction of the diluent reservoir away from the fixed cap extraction member connected to the cap. This allows enclosed opening of a previously sealed diluent reservoir within the barrel of a syringe. In another feature of the invention, the cap extraction member includes flow channels for allowing passage of the mixed drug solution by the cap extraction member and out the syringe. In another feature of the invention, sealing occlusion of the distal tip of the syringe is provided so that negative pressure induced within the syringe withdraws fluid from a compartment proximal to the distal tip of the syringe, thereby withdrawing fluid into the syringe without the need for the fluid to be external and in fluid communication with the distal tip of the syringe. In another feature of the invention, the: reservoir of fluid can carry a drug vial engaging member for connecting the drug vial to the diluent reservoir to allow free mixing between the drug vial and the diluent reservoir so that after the drug has been mixed with the diluent, the cap can be extracted by the cap extracting member and the mixed drug solution can be withdrawn into the syringe by negative pressure induced within the syringe barrel. These and other features will become evident from the summary and detailed description described below. Furthermore, these and other objects and advantages of the invention will be further set forth in the description which follows and, in part, will be learned from the description or may be learned by practice of the invention. The objects and advantages of the invention may be realized by means of the instrumentalities and combinations particularly pointed out in the appended claims.

BRIEF DESCRIPTION OF THE DRAWINGS

FIG. 1 is an exploded view, in partial cross-section, of a syringe according to the present invention;

FIG. 1A is a top plan view of a distal stopper;

FIG. 1B is a bottom plan view of a distal stopper of FIG. 1A;

FIG. 1C is a cross-sectional view of the proximal and distal stopper and connecting tether;

FIG. 4A is a partial cross-sectional view similar to FIG. 3A, showing the plunger being retracted;

FIG. 4B is a partial cross-sectional view similar to FIG. 3A, showing the tether fully extended;

FIG. 4C is a partial cross-sectional view similar to FIG. 3A, showing a repositioned proximal stopper which is advanced relative to the retracted drug vial;

FIG. 6 is an exploded view, in partial cross-section, of another syringe embodiment of the present invention;

FIG. 6A is a top plan view of a distal stopper;

FIG. 6B is a bottom plan view of a distal stopper;

FIG. 6C is an enlarged cross-sectional view of a proximal stopper;

FIG. 6D is an enlarged cross-sectional view of the distal stopper;

FIG. 7A is a cross-sectional view of a vial piston open and ready to be filled;

FIG. 7B is a partial cross-sectional view of the vial piston of FIG. 7A, mounted on a handle in a closed and sealed condition;

FIG. 7C is a top plan view of a sterile package for enclosed assembly and aspiration;

FIG. 9 is an exploded view in partial section of another embodiment according to the present invention;

FIG. 9A is a top plan view of a distal stopper in the embodiment shown in FIG. 9;

FIG. 9B is a bottom plan view of the distal stopper, shown in FIG. 9A;

FIG. 9C is a cross-sectional view of a distal stopper, taken along lines 9C—9C of FIG. 9B;

FIG. 9D is a top plan view of a proximal stopper in the embodiment of FIG. 9;

FIG. 9E is a cross-sectional view taken along lines 9E—9E of FIG. 9D;

FIG. 9F is a cross-sectional view of the proximal and distal stopper used in FIG. 9 when interengaged during operation;

FIG. 11A is a partial cross-sectional view of the syringe of FIG. 9 with the drag vial fully retracted;

FIG. 11B is a partial cross-sectional view of the syringe of FIG. 9 with the drag vial partially advanced as the mixed drag is injected;

FIG. 12A is a partial cross-sectional view of the syringe of FIG. 10 at the initiation of the flush sequence;

FIG. 12B is a partial cross-sectional view of the syringe of FIG. 9 with the plunger fully advanced at the conclusion of the drug injection and flushing;

FIG. 15 is a cross-sectional view of another embodiment of a syringe, according to the present invention;

FIG. 15A is an enlarged cross-sectional view of a portion of the distal end of the syringe of FIG. 15;

FIG. 15B is a cross-sectional view taken along line 15B—15B in FIG. 15A;

FIG. 15C is a cross-sectional view taken along line 15C—15C in FIG. 15;

FIG. 15D is a cross-sectional view of another embodiment having a drag vial sized to be received within the syringe;

FIG. 15E is a cross-sectional view of the embodiment of FIG. 15D, after the stopper has been displaced into the flexible diluent container;

FIG. 15F is a cross-sectional view of the embodiment of FIG. 15D, showing withdrawal of the handle and displacement of liquid from the flexible container into contact with the syringe barrel;

FIG. 17A is a top plan view of a sterile package showing a pleated syringe compartment;

FIG. 17B is a top plan view of the package of FIG. 17A with the syringe handle fully retracted;

FIG. 18A is a cross-sectional view of another embodiment of a syringe, according to the present invention;

FIG. 18B is a cross-sectional view of the embodiment of FIG. 18A with the syringe handle partially retracted;

FIG. 18C is a cross-sectional view of FIG. 18B across lines C—C;

FIG. 18D is a cross-sectional view of the embodiment of FIG. 18A with the handle fully retracted, demonstrating positive drug expulsion and conversion of the open-ended drug vial into a closed-ended piston;

FIG. 18E is a cross-sectional view of the embodiment of FIG. 18A with the handle partially advanced after complete retraction, demonstrating drug solution injection by the now closed-ended drug vial.

DESCRIPTION OF THE PRESENTLY PREFERRED EMBODIMENTS

Figure 2:
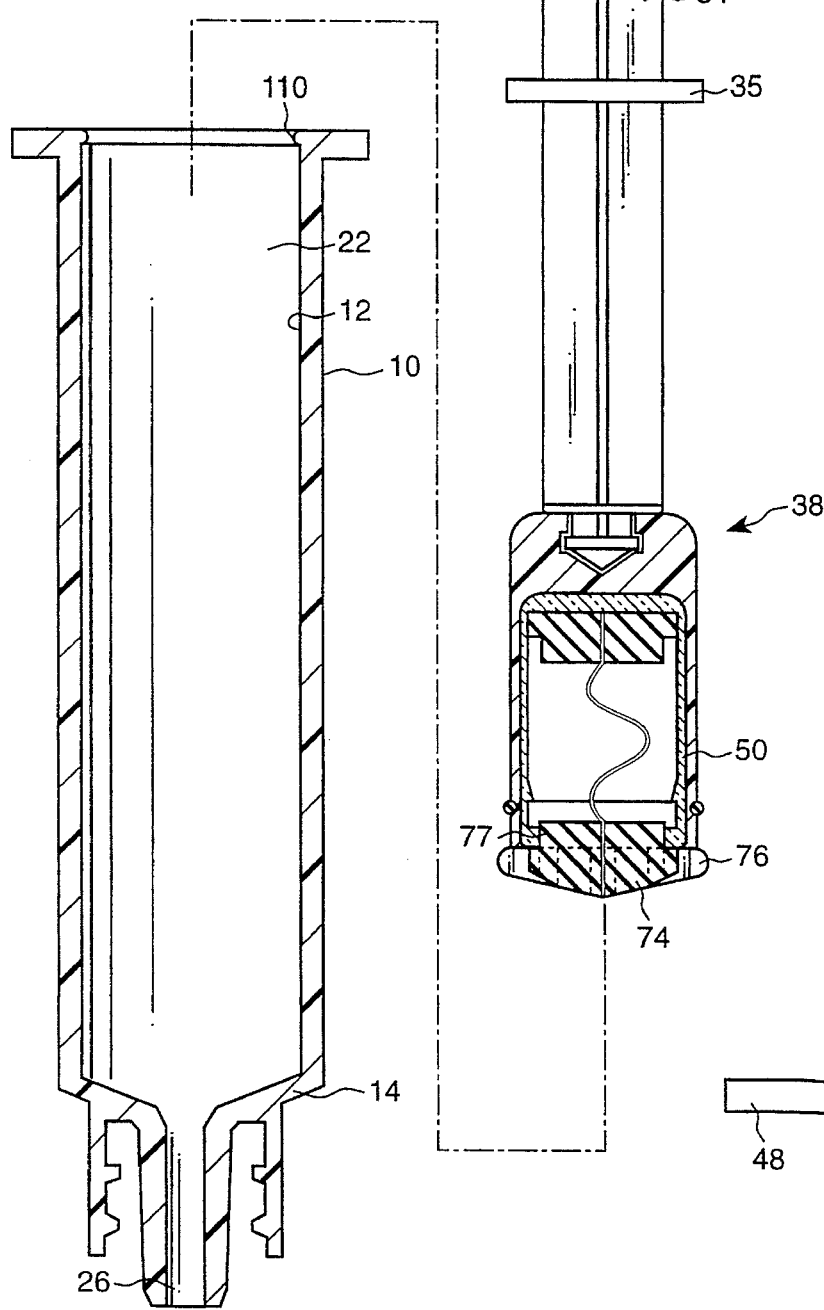
FIG. 2 is an exploded view, in partial cross section, of a syringe according to the present invention.

For more easy understanding of the preferred embodiments, reference can be made to the aforementioned copending patent application which utilizes, for continuity and convenience, many similar figures and numbers to the presently disclosed invention. With reference to one preferred embodiment of the instant invention, a drug-mixing and injection syringe 5 (shown disassembled in FIG. 1) has syringe barrel 10 with inner wall 12 and smooth barrel bore 22. The barrel 10 extends to distal tapered end 14. The syringe 5 has a distal tip 18 and distal conduit 26 in fluid connection with bore 22. The syringe 5 further includes handle 34 having a stop 35. A main vial piston 38 is provided including an outer housing 39 and having a distal sealing cover 45 and weakened tear regions 46, and projecting tear tab 48 enclosing a vial 50 having a vial chamber 51 having an inner wall 52 and an outer wall 53. The vial 50 is preferably made of glass. The housing 39 and cover 45 can be comprised of polypropylene or other suitable material. The main vial piston 38 further includes an annular wiper or O-ring 54 for sealingly engaging wall 12 of bore 22. The vial 50 includes a closed proximal end 55 and a distal open end 60. The vial 50 contains a stopper piston assembly 68, including proximal piston 70 and distal stopper 74. The vial piston 38 further includes handle receiving recess 79 for receiving handle distal end 80, as shown in FIG. 1C. Piston 70 and stopper 74 are connected by a tether portion 84 that includes a tether vent channel 86 extending between a proximal vent portion 87 and a distal vent portion 88. Stopper pistons 70 and 74 are preferably comprised of conventional rubber stopper material. The tether 84 is likewise comprised of conventional rubber so that it is compatible with a variety of drugs and is flexible and capable of transmitting tensile force. A silicone tubular rubber insert (not shown) may be used if desired within the tether 84 to provide added strength and reduce stretching. Distal stopper 74 includes a distal face 75 and a lateral projecting portion 76 and a proximal vial sealing portion 77. The wall portion 76 projects beyond the diameter of distal opening 60 and the outer vial wall 52 of the drug vial 50 and includes multiple lateral flow channels 78 extending through the wall 76 and over the face 75. These flow channels do not communicate with the vial chamber 51 since a distal opening 60 of vial 50 is sealed by the side wall of sealing portion 77. Therefore, flow channels 78 do not require a valve or other means for closure when the chamber 51 is sealed by the stopper 74, thereby reducing both the cost of manufacture and the operating complexity. The vial sealing portion 77 seals tightly about the distal vial end 60. The flow channels 78 are formed by the stopper 74 and the barrel wall 12, but can otherwise be provided entirely through the stopper 74.

In assembly, the proximal piston 70 is fully advanced against the closed proximal end 55 of the vial 50. At this time, as shown in FIG. 7A, the tether 84 which preferably is longer than the vial 50 extends out the open end 60 of the vial 50 and the distal stopper 74 is preferably positioned away from the open end 60 of the vial 50 so that the vial 50 can be filled with a powder or liquid drug. Once the drug vial 50 is filled with powder or liquid drug, the vial sealing portion 77 of distal stopper 74 can be slightly compressed and inserted into the open distal end 60 of the drug vial 50 to provide a tight sealing fit. Vial 50 further includes annular retainer 94, and proximal piston stop 96 for tightly retaining the proximal piston 70 in the fully advanced position, as will be described.

Figure 2A:
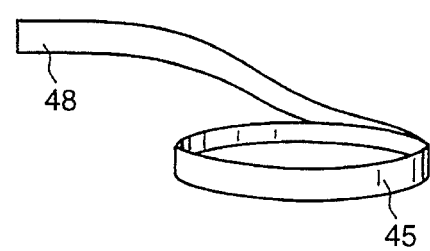
FIG. 2A is a perspective view of the detached vial piston end cover.
Figure 3A:
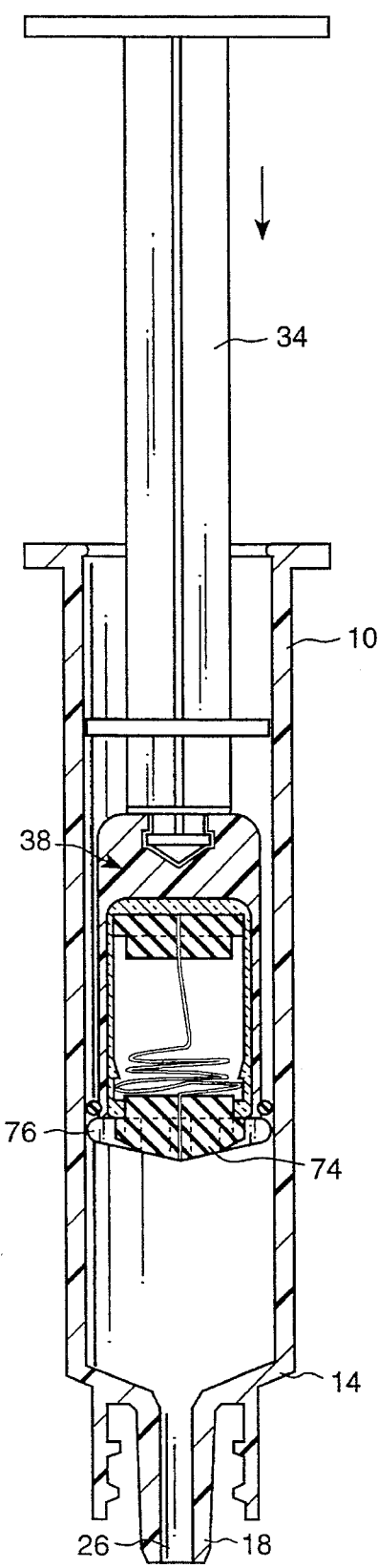
FIG. 3A is a partial cross-sectional view of the syringe as the plunger or vial piston is being inserted into the barrel.
Figure 3B:
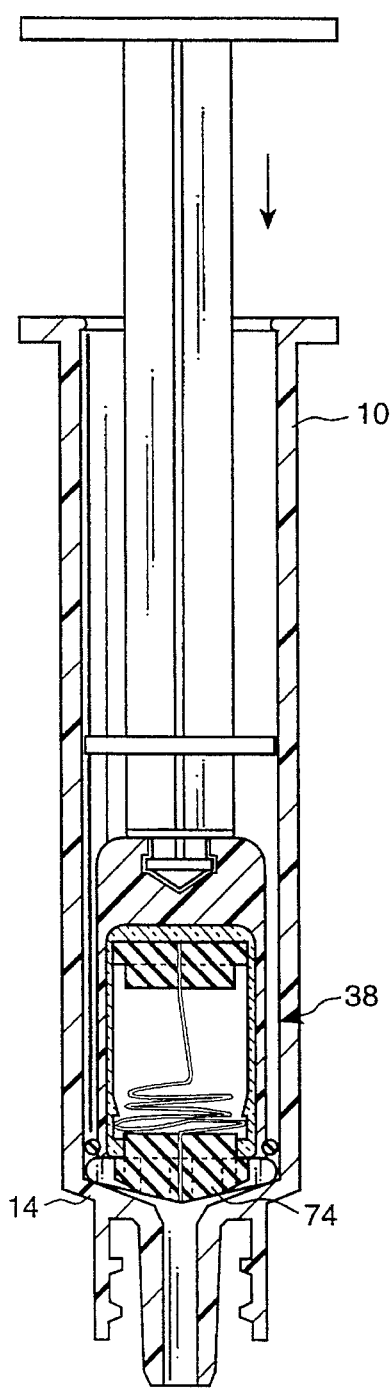
FIG. 3B is a partial cross-sectional view similar to FIG. 3A, with the plunger fully inserted into the barrel.

In operation, when mixture of the drug with a diluent is desired, the cover 45 (FIG. 2A) is removed by removing tear tab 48, the vial piston 38 is then inserted into barrel 10 (FIG. 3A) and fully advanced against the end 14 of the barrel 10 (FIG. 3B). The distal stopper 74 is radially compressed by the barrel wall 12 to provide a tight friction fit and to fix the stopper 74 in the fully advanced venting position, as shown in FIG. 3B. The distal conduit 26 is then placed in fluid communication with a source of diluent, (such as that shown in FIG. 8B), if a source of diluent is not already attached adjacent the distal end 18 of the syringe. The handle 34 is then retracted (FIG. 4A). As the handle 34 is retracted, the drug vial 50 is extracted away from the distal stopper 74 since the distal stopper 74 is tightly held by tight compressive frictional engagement of the laterally projecting portion 76 with the barrel wall 12.

The retraction of the vial 50 forms a nascent mixing chamber 90 intermediate the vial 50 and the distal stopper 74. The displacement of the distal stopper 74 out of sealing engagement with vial opening 60 completely opens the vial chamber 51 into the enlarging nascent mixing chamber 90.

Figure 5A:
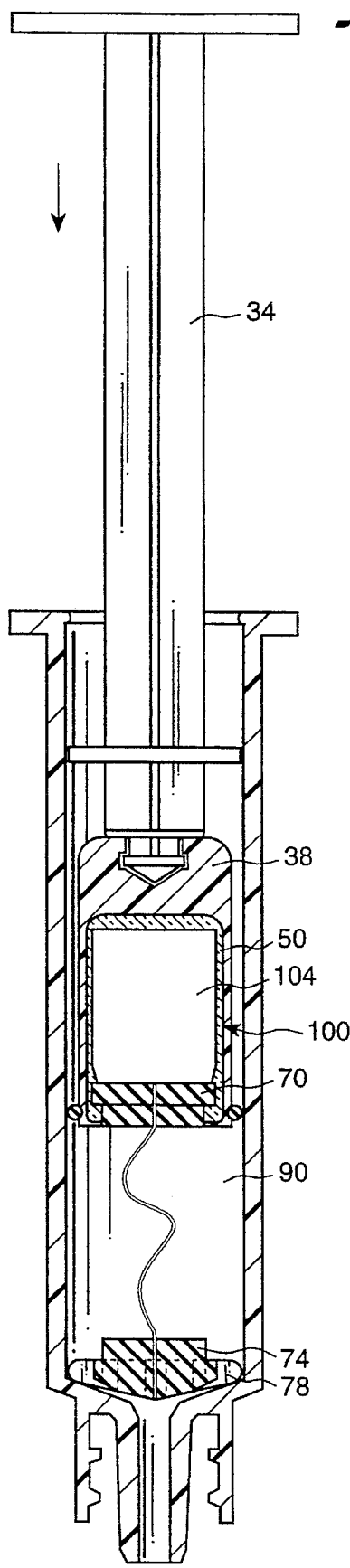
FIG. 5A is a partial cross-sectional view similar to FIG. 3A showing the plunger in an injection mode.
Figure 5B:
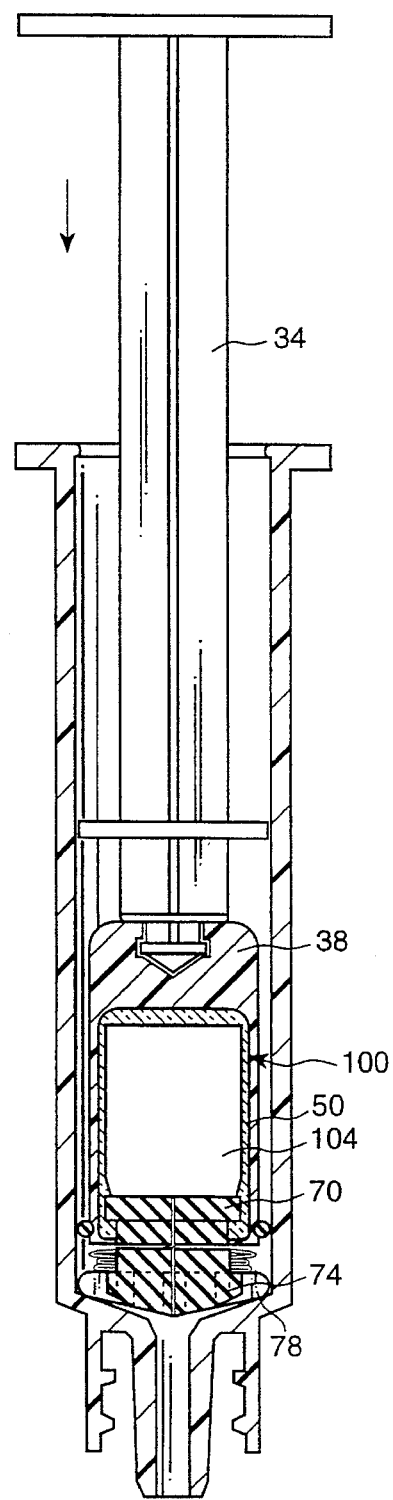
FIG. 5B is a partial cross-sectional view similar to FIG. 3A, showing the completion of the injection.

During this time, the negative pressure within the mixing chamber 90 caused by retraction of the handle 34 causes diluent fluid to pass through conduit 26, through the flow channels 78 of the distal stopper 74 and on into the mixing chamber 90. As the mixing chamber 90 is enlarged, continued circumferential fluid flow enters the mixing chamber 90 through the flow channels 78. As the handle 34 is further retracted, tether 84 becomes fully extended, as in FIG. 4B. After tether extension, further retraction of the handle 34 causes the vial 50 to be moved relative to the now fixed proximal piston 70 so that the proximal piston 70 advances and slides along inner wall 52 relative to the vial 50, thereby reducing vial chamber 51. This expels any liquid or solid contents held within vial chamber 51 into the mixing chamber 90. When piston handle 34 has been fully retracted (FIG. 4C), proximal piston 70 engages stop 96 and is retained within the distal end 60 of the drug vial 50 by stop 96 and by retainer 94. In this position,, as in FIG. 4C, proximal piston 70 now functions as a stopper and sealingly occludes distal end 60 of drug vial 50, thereby converting the formerly widely open drug vial 50 into a closed injection piston 100 (FIG. 5A and FIG. 5B). During relative advancement of the proximal piston 70 along vial wall 52, fluid can flow through the tether vent channel 86 from the conduit 26 into the enlarging reservoir 104 proximal to the piston 70 within vial 50. This will fill the reservoir 104 with diluent. The syringe 5 can then be rocked or rolled to facilitate mixing. Gas can be initially provided in the vial 50 with the drug during initial manufacture and filling to enhance mixing after expulsion of the air from the vial chamber 51 along with the drug into the mixing chamber 90. All of the drug and solution is now contained within the mixing chamber 90 and, therefore, should be visible through the barrel 22, which is preferably comprised of relatively transparent polypropylene. This is advantageous since residual clumps of powdered drug might otherwise be contained within the drug vial 50 and adequate mixing would not, therefore, be easily confirmable by visible inspection.

Some air, which was formerly present in the distal conduit and/or the drug vial chamber 51 will also be present within the mixing chamber 90 and will also allow for agitation of the mixing chamber 90 to assist in mixing of the drug and diluent.

To further facilitate adequate mixing, the syringe can be positioned so that the distal tip 18 is in an upward position and the handle 34 can be moved back and forth to facilitate mixing. Retraction of the handle 34 is preferably limited by a proximal handle detent 110 along barrel 10 which is positioned so that tether 84 is fully extended when proximal detent 110 is engaged by the handle stop 35. This engagement prevents excessive tensile force from being transmitted to the rubber tether 84 and assists in fixing the volume of diluent for mixing with the drug.

Once adequate mixing has been achieved and with the distal tip 18 in the upright position, any residual air can be expelled. The drug solution can then be injected (as depicted by the arrows (in FIG. 5A and FIG. 5B) or the syringe 5 can be capped for transport from the pharmacy to the nursing station for subsequent use.

In a preferred embodiment (shown in FIG. 7C), the syringe barrel 10 and the piston handle 34 and vial piston 38 are enclosed within a single sterile flexible plastic envelope 120 in an unassembled configuration with an attached cannula 122 and a cannula cover 124. The plastic envelope 120 is preferably of conventional flexible transparent and medically sterilizable material, such as polyethylene or polyvinylchloride, so that the syringe handle 34 and syringe barrel 10 may be manipulated within the material for enclosed assembly within the envelope 120. In operation, the projecting tear tab 48 is grasped by the thumb and forefinger through the flexible envelope 120 and the tear tab 48 is held in position while the syringe handle 34 is rotated until the cover 45 is separated from the vial piston 38. The tear tab 48 can be 1.5–2 centimeters or larger in length to provide ease in grasping through the envelope 120. The handle 34 and the barrel 10 are then grasped and aligned within the envelope 120. The envelope 120 is provided with sufficient length so as to allow room for such alignment. The handle 34 is then inserted into the barrel 10 and advanced until the distal stopper 74 engages the distal end 14, as previously discussed. Assembly is then complete. The envelope 120 can then be opened, removed, and the conduit 26 placed in fluid communication with a source of diluent for aspiration of diluent into the syringe 5.

Alternatively, as in FIG. 7C, envelope 120 can include a compartment 130 containing a sterile diluent, such as a saline or dextrose solution, and a syringe compartment 140 containing the syringe 5 components separated from the fluid compartment 130 by a thermoformed seal or bond 145. A membrane or septum 146 intermediate the compartments can be provided for penetration by the distal tip 18 or an attached cannula 122 so that diluent could be directly aspirated from within the diluent compartment 130 and so that the entire process could be accomplished within a completely enclosed sterile environment. Alternatively, an inexpensive diluent container, as for example, a molded polypropylene bottle (not shown) can be enclosed with the syringe components in the main envelope 120.

In a further embodiment (not shown), the syringe tip 18 may be sealingly capped and packaged with the distal tip 18 projecting into, and sealed within, the diluent or fluid compartment 130. This allows simplified packaging by placing the syringe tip 18 in a position such that the dividing seal 145 between the syringe compartment 140 and the diluent compartment 130 extends across and includes the distal tip 18. With this embodiment, the fluid compartment 130 may be only partially distended so that the syringe cap or cover 124, which can include an additional sealing cover (not shown), can be easily grasped through the fluid and envelope 120 and removed to unseal conduit 26 at tip 18 when aspiration of fluid is desired. Once disengaged from tip 18, the cap or cover 124 can be discarded within the compartment 130.

This comprehensively enclosed system is especially useful when the contained drug is a chemotherapeutic agent, thereby greatly eliminating occupational exposure of even minute amounts of chemotherapeutic drugs wherein cumulative occupational exposure may be hazardous to the healthcare worker. It is further advantageous to utilize such assembly of the syringe 5 within envelope 120 when the syringes are being prepared and the drugs are being mixed within the syringes at a site remote from the site of the syringes intended use or when there will be a significant delay between assembly and use. Examples include home healthcare, mobile intensive care units, emergency medicine mobile units, and in hospitals when preparation is performed in a centralized pharmacy for distribution to floor units.

It can be seen that unless subsequent resterilization is contemplated, assembly of a syringe utilizing a sterile piston and handle and a sterile barrel must be accomplished with care and generally must be accomplished with sterile gloves and masks. This is so since contact or droplet contamination of the handle could subsequently result in contact contamination of the barrel, which later may be filled with solution, thereby resulting in contamination of the solution. In addition, during storage, organisms can potentially enter a stored assembled syringe from the barrel side and contaminate the syringe, especially if use of the syringe is delayed. It would therefore be preferable, in situations described above, that the syringe be assembled and the drug mixed with solution while the syringe is maintained within the original sterile container. This effectively eliminates the need to repackage the syringe for later use, minimizes packaging cost and expense, and further eliminates the need for assembly personnel to wear masks and gloves while handling the syringe and substantially reduces the risk of potential for exposure of the assembly personnel to drugs or other potentially toxic material which may be reconstituted within the syringe. It should also be noted that liquid other than a diluent can be utilized and withdrawn into the syringe. For example, a drug solution which can subsequently be mixed with the powdered or liquid drug within the vial can be provided and subsequently drawn into the syringe for mixing, as described for the diluent.

Figure 8A:
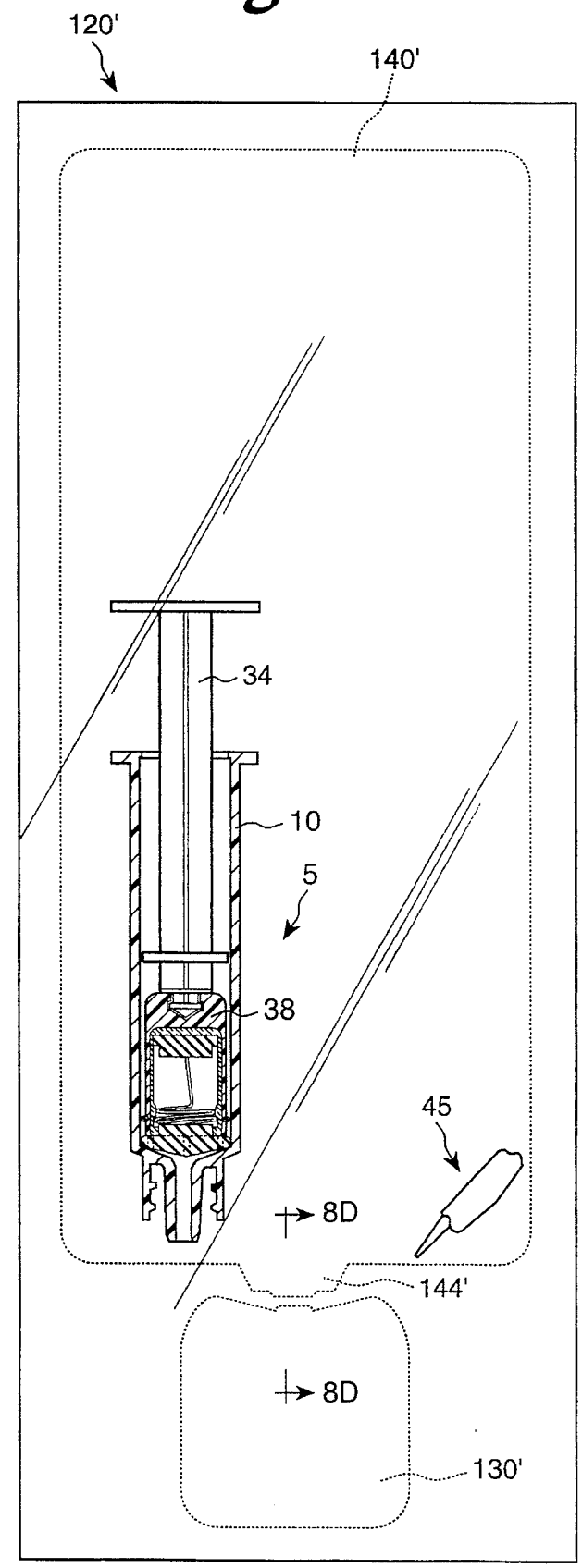
FIG. 8A is a top plan view of another embodiment of a sterile packaging system, according to the present invention, showing a syringe compartment and a liquid compartment.
Figure 8B:
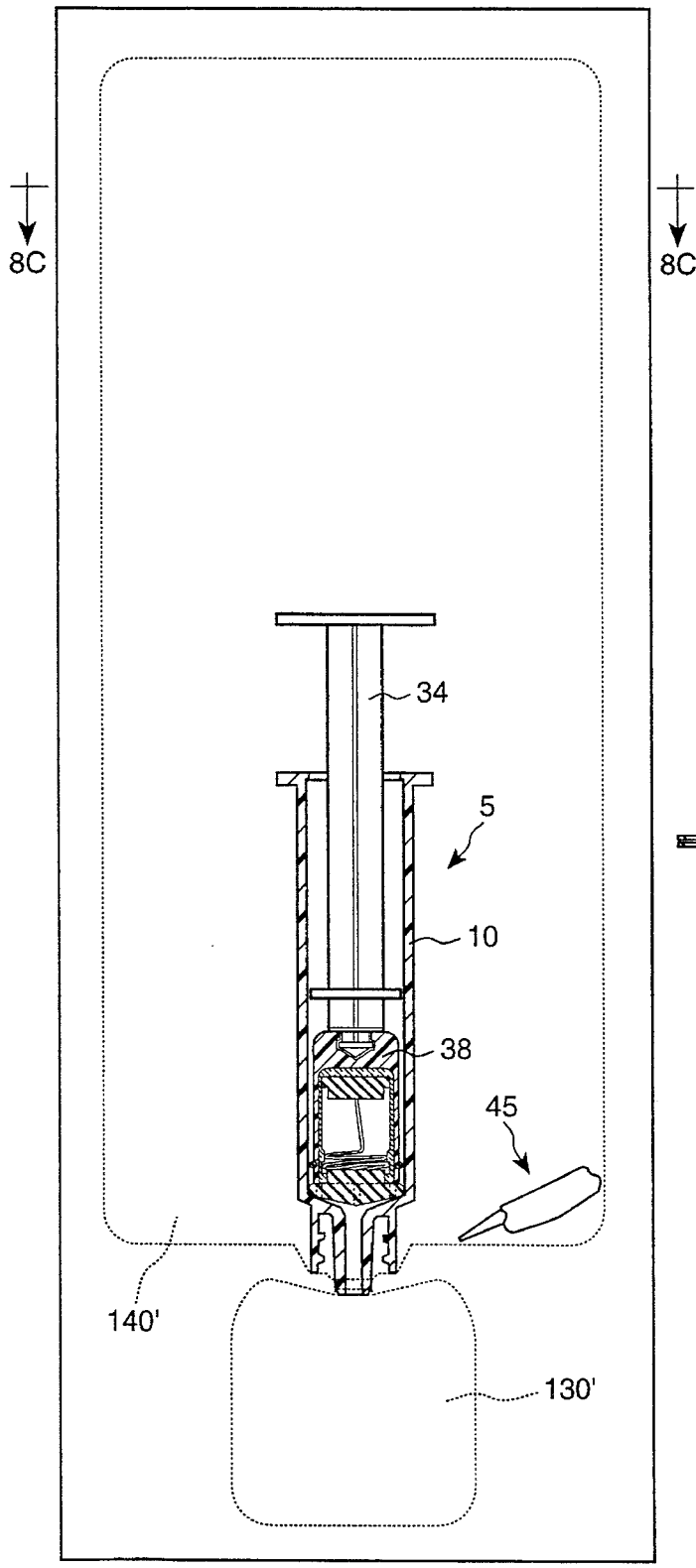
FIG. 8B is a top plan view similar to FIG. 8A, showing the syringe tip advanced through a weakened sealed section in the package.
Figure 8C:
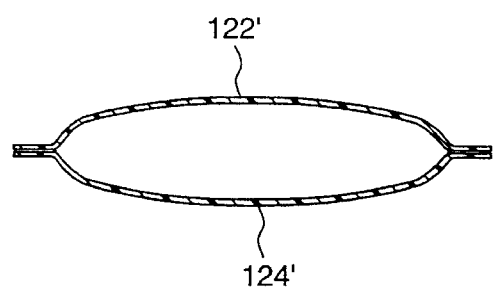
FIG. 8C is a cross-sectional view of the package, through lines 8C—8C, showing the upper and lower planar members.
Figure 8D:
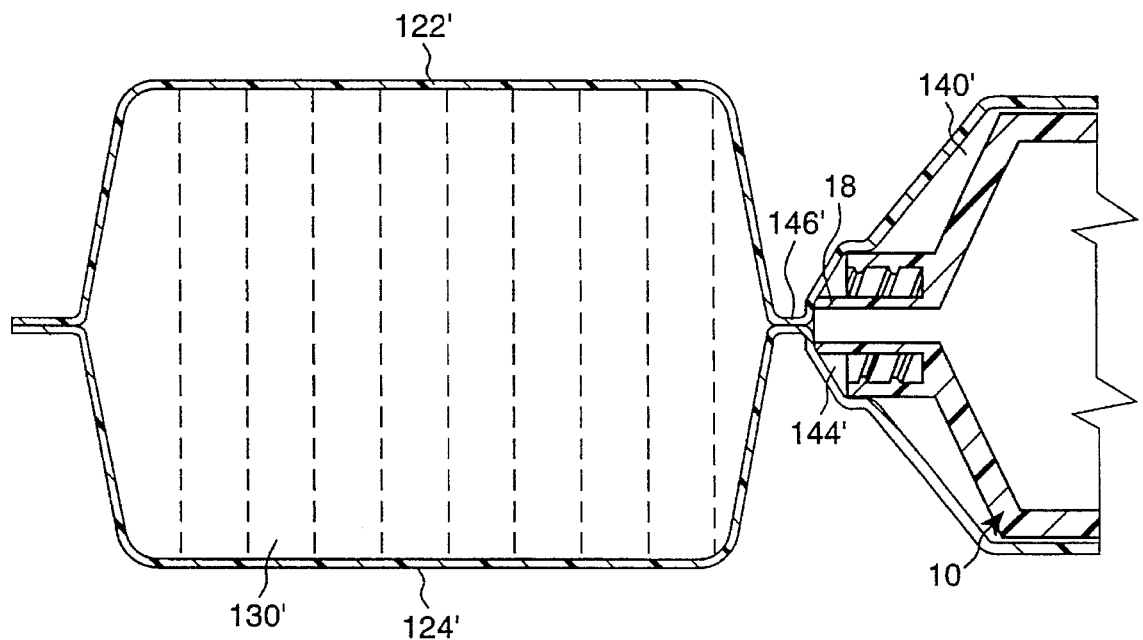
FIG. 8D is a cross-sectional, view through lines 8D—8D, showing the weakened section between the fluid compartment and the syringe compartment, engaged by the distal tip of the syringe.
Figure 8E:
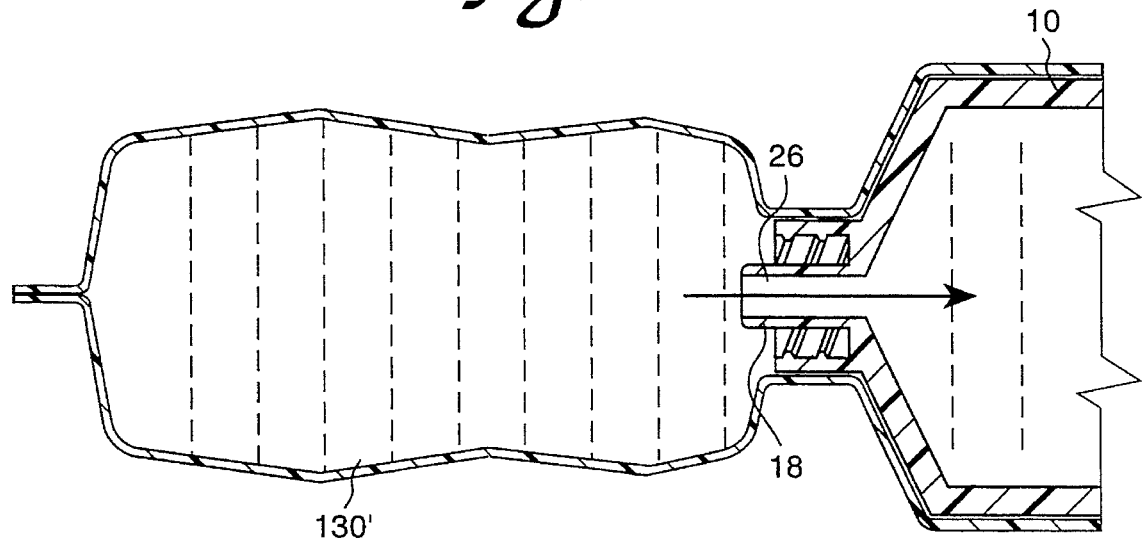
FIG. 8E is a cross-sectional view, similar to FIG. 8D, showing the syringe tip pushed through the weakened section to enter the fluid compartment.

In a further embodiment (as shown in FIG. 8A) for inexpensive enclosed packaging and preparation, the syringe 5 is shown after assembly within a sealed, sterile transparent envelope 120' with the cover 45 removed from the vial piston 38 and the vial piston 38 inserted into the barrel 10. Envelope 120' includes a syringe chamber 140' and a liquid chamber 130'. The envelope 120' is preferably comprised of two planar sheets (FIG. 8C) of polyvinyl chloride, an upper sheet 122' and a lower sheet 124'. These sheets are bonded or thermoformed to enclose the syringe compartment 140' and the liquid compartment 130'. A recess 144' is provided intermediate the liquid compartment 130' and the syringe compartment 140'. A weakened sealed region 146' (shown in FIG. 8D) is provided adjacent the liquid compartment 130' and the recess 144'. In operation, after the cover is removed from the vial piston 38 and the vial piston inserted into the barrel 10. Then, shown in FIG. 8D and FIG. 8E, the syringe tip 18 may be inserted into the recess 144' and subsequently wedge apart the weakened region 146' to enter the liquid compartment 130'. At this time, the handle 34' can be retracted to draw fluid into the syringe 5. If preferred, another envelope 120" (such as is shown in FIG. 17A) can be provided with a pleated, bunched, folded portion 150", or otherwise redundant portion to facilitate retraction of the handle 34. A tear or weakened portion 121" can be provided so that the envelope 120" can be removed once the fluid has been withdrawn into the syringe 5 and the drug properly mixed with the fluid. It can be seen that utilizing this comprehensive packaging system, the entire process can be complete without exposing the syringe 5 to potential contamination to the environment and without exposing the preparing personnel to even minute quantities of drug.

Another preferred embodiment is shown in FIG. 6. This embodiment utilizes a cylindrical drug vial 50' which is open at the distal end 60' and the proximal end 55'. A distal piston 74' having circumferential flow channels or slots 78', as described for the previous embodiment, is sealingly received into the distal end 60' of vial 50'. A proximal piston 70' includes a handle recess 79' for threadingly receiving a threaded end 80' of syringe handle 34'. The proximal piston 70' is sealingly received into the proximal end 61'. A cover 45' having weakened areas 46' and a tear tab 48' is provided over the proximal piston 70' and extends over the distal stopper 74'. Upon removal of the tear tab 48' along the weakened areas 46', the entire cover 45' can be removed from the vial piston 38'. Alternatively, separate proximal and a distal covers (not shown) could be provided with two separate tear tabs. A barrel 10' is provided with bore 22' having interior wall 12' for receiving the vial piston 38'. A stop 35' can be provided on handle 34' to preset the volume of diluent to be aspirated into the barrel 10', as will be described.

In assembly, a covered drug vial piston assembly 38', the handle 34', and the barrel 10' are preferably enclosed within a sterile envelope, as previously shown in FIG. 7C. If desired, at least one portion of the envelope can include a region permeable to gas, such as Tyvek™, (not shown) for gas sterilization, as is known in the art. As noted previously, the sterile envelope is flexible and comprised, for example, of a material such as polyethylene or polyvinyl chloride, so that the components within the envelope can remain sterilely sealed yet be easily grasped, manipulated, and assembled therein.

In operation, the tear tab 48' is grasped and the tear tab 48' and cover 45' are removed from the vial piston assembly 38' The handle 34' is then inserted into recess 79' which can be threaded, as shown, to receive the handle end 80' without substantial longitudinal force exerted against the proximal piston 70'. If preferred, the tear tab 48' is located adjacent proximal piston 70' of the vial piston assembly 38' so that the proximal portion of the cover 45' could first be removed, handle 34' threadably received into the recess 79', and handle 34' grasped for more easy removal of the distal portion of the cover 45' through a flexible envelope (such as is shown in FIG. 8A). Once the entire cover 45' is removed, the piston assembly 38' and its attached handle 34' are inserted into the barrel 10' and fully advanced to the end of the barrel 14'. As described in the previous embodiment, the projecting lateral wall 76' of distal stopper 74' is of greater diameter than the barrel bore 22' so that the lateral wall 76' can be pressed very tightly against the interior wall 12' of the barrel 10'. This assures a tight friction fit between the distal stopper 74' and the barrel 10' so that, while the piston 74' can be slidingly advanced by force along the barrel 10' to the distal end 14'. Once positioned at the distal end of barrel 10', piston 74' will stay in place. Consequently, upon retraction of the handle, vial 50' will be extracted away from the distal stopper 74' since the position of distal stopper 74' is fixed by the tight fit against the barrel wall 12'. As the handle 34' is retracted, the distal end 60' is pulled away from stopper 74', thereby widely opening drug vial 50' and forming a mixing chamber intermediate the open-ended drug vial 50' and the distally retained distal stopper 74', as described and shown in the previous embodiments.

During this time, fluid can flow through the flow channels 78' adjacent the distal stopper 74' to fill the mixing chamber and to mix drug with the fluid entering through the flow channels 78'. When the handle 34' syringe has been fully retracted to draw the desired fluid volume into the syringe, the syringe can be agitated to mix the drug with the fluid. The syringe conduit 26' can then be placed in fluid connection with the intended recipient of the drug and the piston handle 34' can be advanced. As piston handle 34' is advanced, fluid exits the flow channels 78' adjacent the distal stopper 74'.

The proximal piston 70' can be sized so that the frictional fit against vial wall 52' induces less resistance to advancement than the frictional fit of the wiper 54' against the inner barrel wall 12'. Therefore, upon advancement of the handle 34', the proximal piston 70' first advances along vial wall 52' until it is fully advanced to seal the distal end 60' of vial 50'.

Retaining detents 94' can be provided to retain the proximal piston 70' in its fully advanced position at opening 60' against piston stop 96'. At this time, further advancement of handle 34' will cause the entire vial 50' with fully advanced piston 70' to advance, thereby continuing the injection of fluid from the mixing chamber out the conduit 26' and into the intended recipient.

It is clear that many modifications may be made within the scope of this teaching. For example, diluent could be stored within a portion of the syringe, rather than external to the syringe. A bypass region and detents could be provided along the syringe barrel to provide the flow channel function, positioned at the distal end or midway along the syringe. The syringe handle could be positioned within the barrel during storage. Hooks could be provided along the wall of the syringe for catching the tear tabs upon rotation or advancement of the handle so that the tear tab and sealing cover is automatically displaced from the distal end of the syringe upon engagement of the hooks and rotation or advancement of the handle, thereby separating the tight seal between the drug vial and the cover within the syringe barrel. A tether valve can be provided within the distal stopper, as described in the aforementioned Patent Application ™08/196,455 to allow a flow channel through the distal stopper when the distal stopper is fully advanced against the end of the syringe. The sealing fit of the distal stopper can be adjusted so that it is quite tight and the sealing fit of the proximal piston within the drug vial can be adjusted so that it is quite loose, thereby assuring that the distal stopper will be retained in the distal end as the tether pulls the proximal stopper piston along the drug vial to expel the drug into the mixing chamber. It can be seen that, with such an embodiment if a tether and a valve are provided, the tether need not be connected to the valve, but rather the valve may be designed to open on contact with the distal end and remain open with the tether being otherwise connected to the upper face of the distal stopper.

Another preferred embodiment, shown in FIG. 9, utilizes the previously described flow of liquid through the vent to allow storage of liquid within a proximal portion of the syringe for subsequent injection after the injection of the drug solution, thereby flushing the syringe and the injection site free of drug solution. A syringe barrel 10" is provided with bore 22" and inner wall 12". The handle 34" continues to include a stop 35". The handle is connected to a vial piston assembly 38" having a polymeric portion 39" and a glass drug vial 50" with a closed proximal end 55" and an open distal end 60". The vial piston 38" includes cover 45" having tear tab 48". The vial piston 38" further includes a thin circumferentially extending rubber wiper sleeve 54". A proximal stopper piston 70" is provided connected by a tether 84" to a distal stopper 74". The distal stopper 74" includes vial sealing portion 77" which seals tightly about inner vial wall 52" at opening 60". The vial sealing portion 77" further includes a series of longitudinal slots 150 which extend to a distal end 156. A projecting wall portion 76" is provided having radially projecting flow channel slots 78". These radial slots 78" are provided about the entire perimeter of the lateral wall portion 76" so as to provide complete circumferential fluid influx for more complete and rapid mixing of drug with the fluid to provide circumferential afflux of fluid to allow the drug solution to exit uniformly, and for the complete circumferential flush of drug solution from the syringe 10".

The proximal piston 70" includes several flow channels 160 and a contact-activated longitudinal slit valve 164 which includes longitudinal slit 168. The entire proximal piston 70", including the slit valve 164, is preferably comprised of conventional rubber stopper material. The slit valve 164 extends to tip 170. The slit 168 is tightly closed at rest, preventing flow of fluid through from channel 160 out slit 168 and further preventing flow in the reverse direction through slit 168 and into flow channel 160.

Slit valve 164 will open upon forceful contact of tip 170 against distal stopper 74", as shown in FIG. 9F. This allows free fluid communication between flow channels 160 and slots 150. The slit valves preferably cannot be completely compressed so as to horizontally close slit 168 even with high pressure against distal piston 74". This can be provided by including thickened walls 166 which provide resistance to excessive longitudinal compression, as shown in FIG. 9F. Further, this provides for a space 180 between proximal piston 70" and distal piston 74", allowing free flow of fluid into longitudinal slots 150, as will be described.

Tether 84", which again includes a tether vent, (as illustrated in previous embodiments), is provided intermediate the proximal piston 70" and the distal piston 74", thereby connecting together the proximal piston vent portion 87" and distal vent portion 88". The distal vent portion 88" can be compressed and closed by radial compression of the vial sealing portion 77", as by sloping inner vial wall 52" adjacent the distal vial end 60" when the stopper 74" is sealingly engaged with the vial 50", as shown in FIG. 9.

Figure 10A:
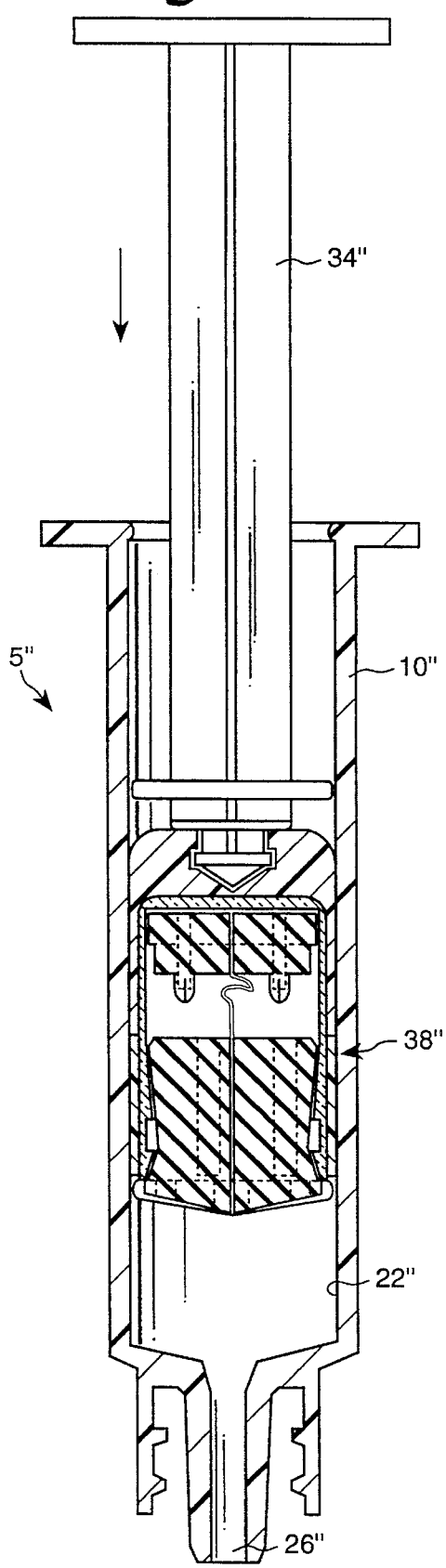
FIG. 10A is a partial cross-sectional view of the syringe of the embodiment of FIG. 9 with the plunger inserted into the barrel.
Figure 10B:
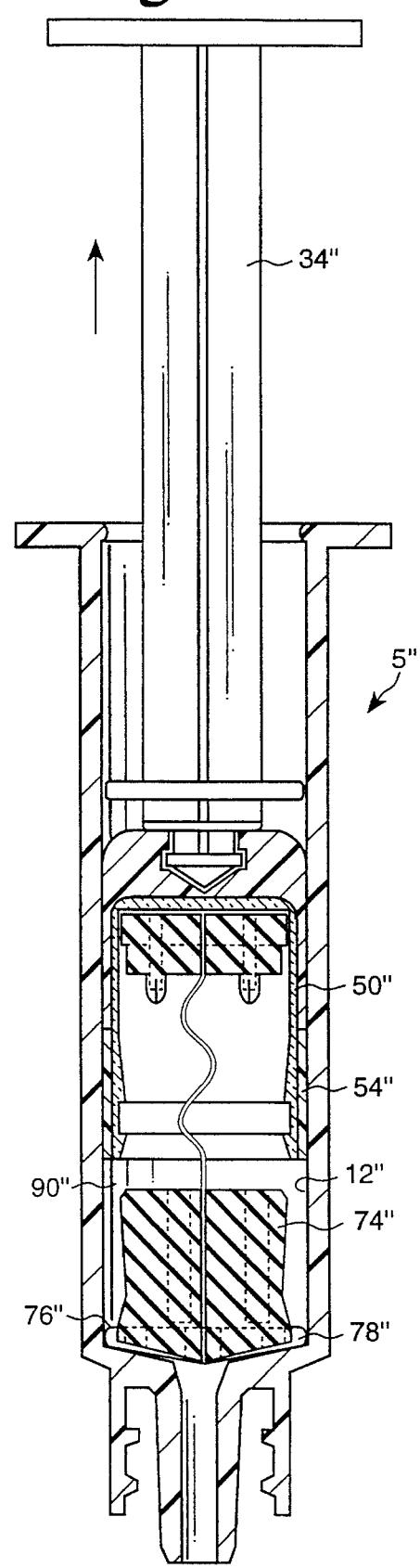
FIG. 10B is a partial cross-sectional view of the syringe of FIG. 9 with the drag vial partially retracted.

In operation, the piston assembly 38" is loaded into the barrel 10" and advanced, as shown in FIG. 10A. Distal conduit 26" is then connected to a source of diluent (if the source of diluent is not already attached to the distal conduit end) and the handle 34" is retracted and the diluent is withdrawn into the syringe 5" since stopper 74" is retained by tight frictional fit with the wall 12" and, thereby the drug vial 50" is extracted away from the stopper 74". As described for the previous embodiments, diluent flows through flow channels 78" defined by wall portions 76" and barrel wall 12" and into a nascent mixing chamber 90". With continued retraction, the tether 84" becomes extended (FIG. 11A), applying tensile force to the proximal piston 70" and effectively advancing the proximal piston 70" along the drug vial 50".

As the proximal piston 70" advances along the drug vial 50", a nascent flush fluid chamber 104" is formed within drug vial 50", intermediate the closed end 55" of drug vial 50" and the proximal piston 70". When aspiration is complete, mixing chamber 90" is filled with diluent and drug and the flush chamber 104" is filled with flush solution. The syringe 5" is now ready for sequential injection and flush, as in FIG. 11B. The distal conduit 26" is placed in fluid connection with a receiver, such as an intravenous saline well, as shown in the aforementioned Patent Application #08/196,455. The handle 34" is then advanced (FIG. 12) and the drug solution is injected into the recipient. The drug solution flows from the mixing chamber 90" through the flow channel slots 78" and out the conduit 26". When slit valve 164 contacts the distal piston 74" (as in FIG. 12A and FIG. 12B), the slits 168 open, allowing fluid connection between space 180 and flush compartment 104" through flow channels 160. As the handle 34" is further advanced, the vial 50" passes over distal stopper 74", pushing proximal piston 70" in a proximal direction, this compresses flush chamber 104" within vial 50" to force fluid out flow channels 160 through slits 168 and into space 180, whereby the fluid flows through the distal stopper slots 150 and the adjacent drug vial wall 52" until the fluid escapes past distal end 60" of the drug vial and out radial slots 78" and distal stopper 74" and then through conduit 26". This effectively flushes the residual drug from syringe 5" and further flushes the distal conduit 26" and its connecting receiver (such as a saline well, not shown) free of drug, thereby completing the drug injection and flush maneuver with a single piston advancement.

Figure 13:
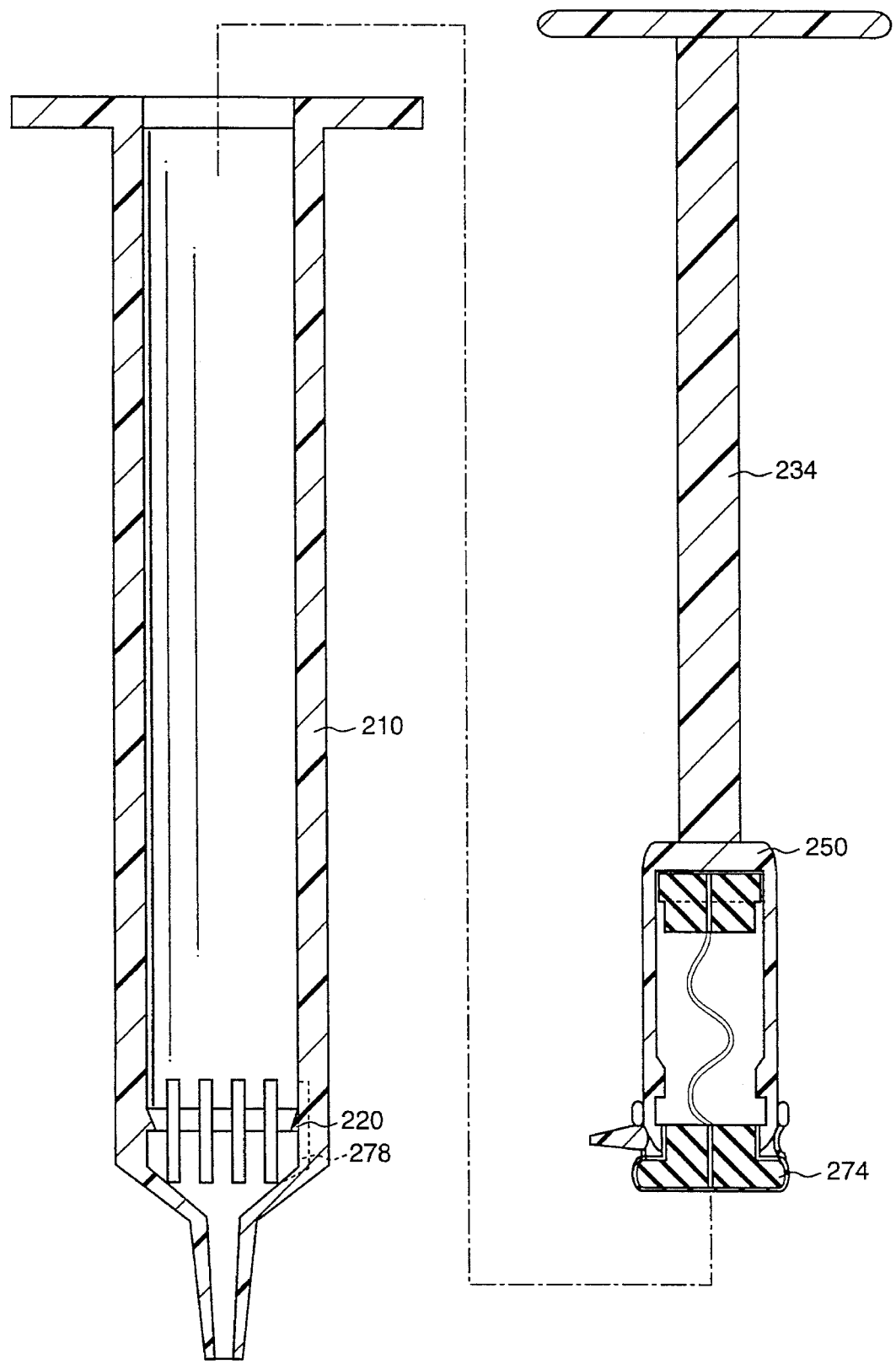
FIG. 13 is an exploded cross-sectional view of a syringe, according to another embodiment of the present invention having an integral drag vial and handle.
Figure 14:
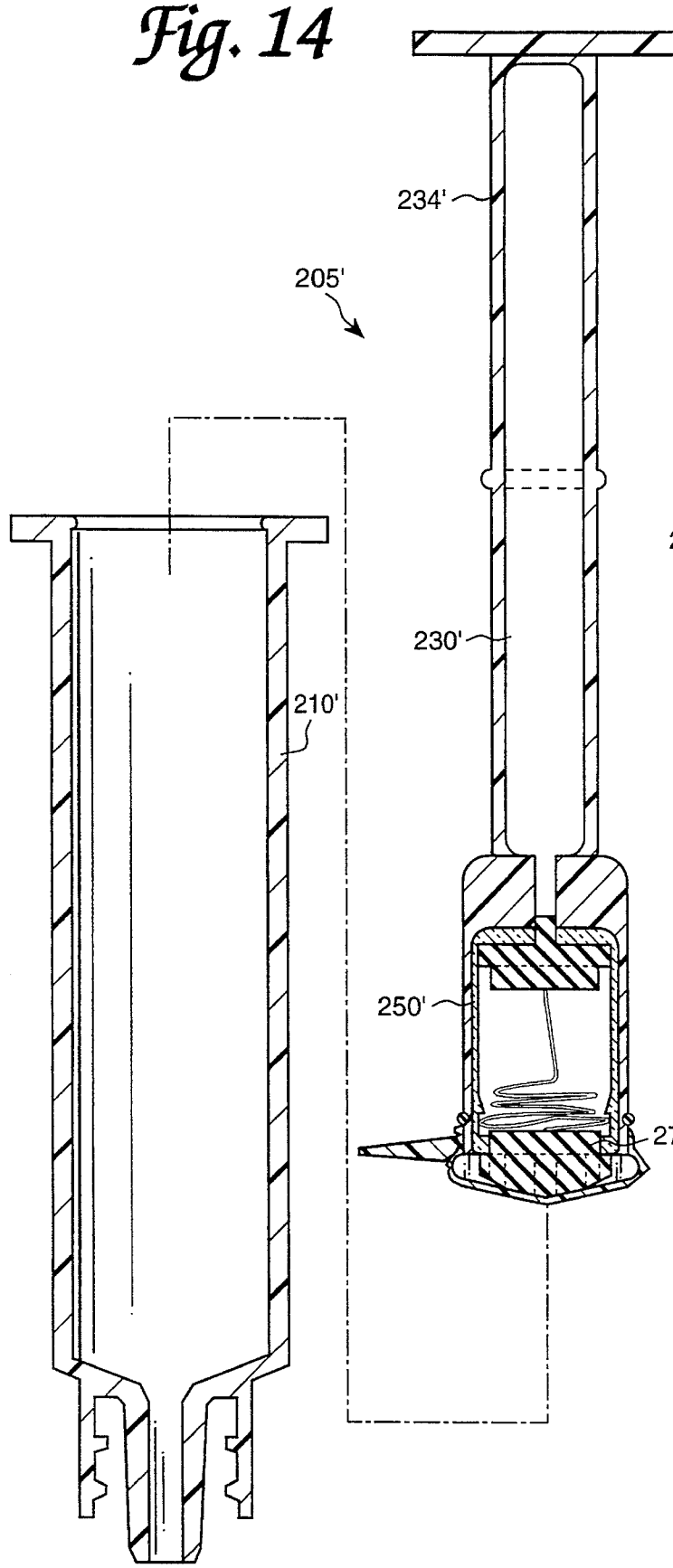
FIG. 14 is an exploded cross-sectional view of a syringe, according to another embodiment of the present invention having a voluminous hollow handle reservoir.
Figure 14A:
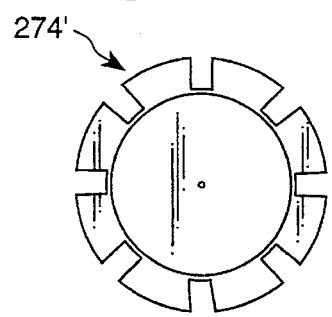
FIG. 14A is a top plan view of a distal stopper in the embodiment shown in FIG. 14.
Figure 14B:
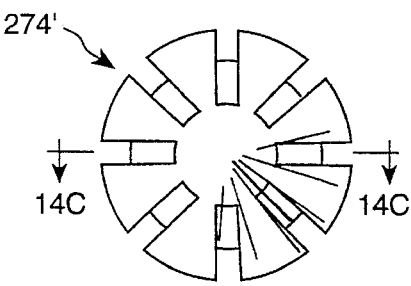
FIG. 14B is a bottom plan view of the distal stopper, shown in FIG. 14A.
Figure 14C:
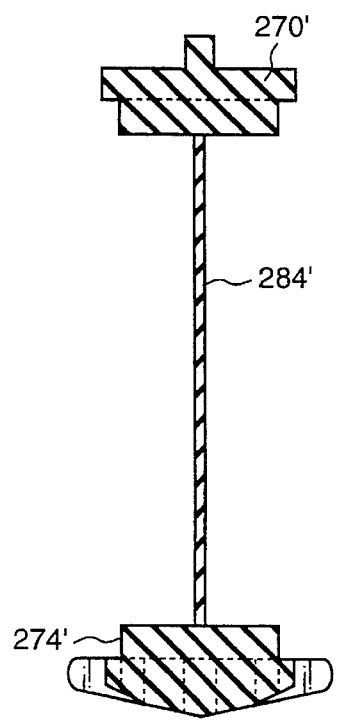
FIG. 14C is a cross-sectional view of the bottom and distal stoppers from the embodiment shown in FIG. 14.
Figure 16:
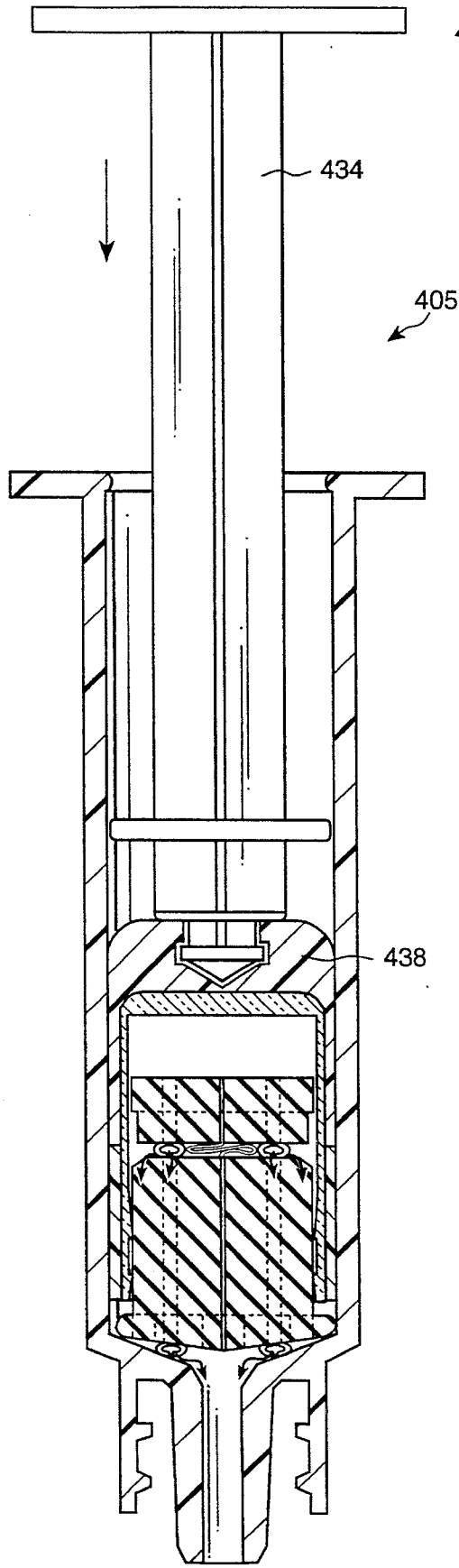
FIG. 16 is a partial cross-sectional view of another embodiment of a syringe, according to the present invention.
Figure 16A:
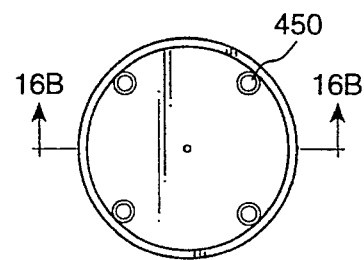
FIG. 16A is a top plan view of a distal stopper used in the embodiment shown in FIG. 16.
Figure 16B:
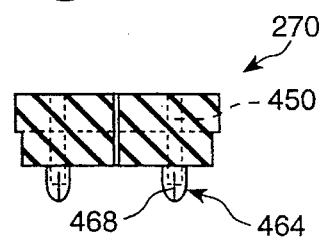
FIG. 16B is a cross-sectional view taken along line 16B—16B in FIG. 16A.
Figure 16C:
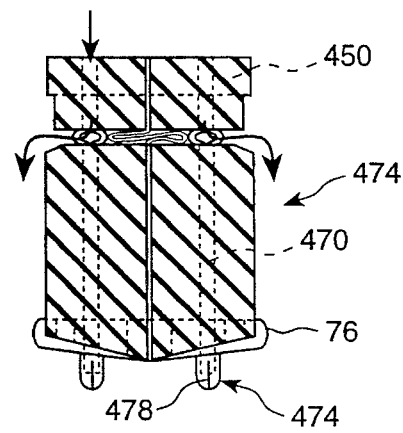
FIG. 16C is a cross-sectional view of the proximal and distal pistons from the embodiment of FIG. 16 when interengaged during operation.

It is clear that many modifications may be made to the aforementioned exemplary embodiments. For example, in another embodiment (shown in FIG. 13), a drug vial 250 is integral with a handle 234 and detents 220 are provided along barrel 210 for retaining the distal stopper 274 in a distal venting position adjacent bypass vents 278. In another embodiment (as shown in FIG. 14), the handle 234' cart be hollow and contain a large sealed chamber 230' which can store and provide the sterile gas or liquid to relieve the negative pressure within the drug vial 250' when the proximal piston 270' is advanced along the drug vial 250'. This eliminates the need for a tether vent in tether 284. The large volume within the handle 234' allows the proximal piston 270' to advance with minimal negative pressure development within the drug vial 250' and handle 234', thereby facilitating ease of advancement while maintaining a sealed environment. The handle 234' could alternatively store flush solution and a one-way valve (not shown) could be provided intermediate the vial 250' and the sealed handle chamber 230' so that fluid transferred into the vial 250' from the handle 234' can later be selectively displaced into the barrel 210', as through slit valves in the proximal piston (as shown in the previous embodiment) for subsequently flushing of the syringe 205' after drug injection. Another embodiment (FIG. 16) shows contact-activated flush valves 464 on both the proximal piston 470 and the distal stopper 274". This type of valve can be used to replace the tether valve of my aforementioned Patent Application #08/196,455.

A further preferred embodiment is shown in FIG. 15. A drug-mixing and injection syringe has a syringe barrel 10''' with inner wall 12''' and a smooth barrel bore 22'''. The barrel 10''' extends to distal tapered end 14''' The syringe 5''' has distal tip 18''' and distal conduit 26''' in fluid connection with bore 22''' The conduit 26''' is occluded by a sealing cap or cover 19. The syringe further includes handle 34''' which includes a pair of opposing rigid support members 300 (which are also shown in FIG. 15C) extending to a distal retainer 310 for connection to the proximal piston 70' '''. The support members 300 extend to a proximal end 320 which is bonded to drug vial receiving member 324 for receiving drug vial 50''' having sealing plug 330. The handle 34''' further includes a flexible diluent reservoir 350 having a distal end 354 and a proximal end 358 and a folded or gathered region 359 adjacent the proximal end 358. The proximal end 358 is occluded by reservoir plug member 360 having a finger contact rim 364 and a including a male vial plug engaging member 368 for retentive engagement with vial plug 330. The support members 300 are spaced apart to define intermediate finger contact windows 366 for allowing direct finger contact of flexible reservoir 350 adjacent contact rim 364 to allow easy displacement of plug 360, as will be discussed.

The flexible fluid reservoir 350 includes a inner chamber 370. The inner chamber 370 is in fluid connection with tube 374 (FIG. 15A), defining a lumen 378 extending to a distal lumen opening 380. A one-way valve 384, shown generically in FIG. 15A, is provided within the lumen 378 for occluding the lumen 378. The one-way valve 384 can be one of any number of conventional one-way valves which are opened by relative negative pressure distal the one-way valve 384 and which are closed by relative positive pressure distal the one-way valve 384. For example, a ball and cage valve, a flap valve (as utilizing a thin, flexible polymeric or rubber flap, the deflection of which is responsive to a pressure differential across the flap), or other conventional valve may be utilized. The lumen 378 of tube 374 is occluded by sealing cap 390 connected to distal stopper 74'''. As described for the previously discussed embodiments, a piston stopper assembly 68''' is provided and shown enlarged in FIG. 15A. The piston stopper assembly 68''' includes distal stopper 74''' and proximal piston 70'''. Prior to use, distal stopper 74''' and proximal piston 70''' are connected by tube 374, which thereby comprises a connecting element. As with the previous embodiments, distal stopper 74''' includes radial flow channels or slots 78'''. The distal stopper 74''' has a diameter which is greater than the diameter of bore 22''' so that distal stopper 74''' is compressably received within bore 22''' to provide a tight frictional fit against inner wall 12''' Distal stopper 74''' is, therefore, fixedly engaged with inner wall 12''' after distal stopper 74''' has been forcibly advanced to the maximum position within the barrel 10''' adjacent barrel end 14'''

Figure 15G:
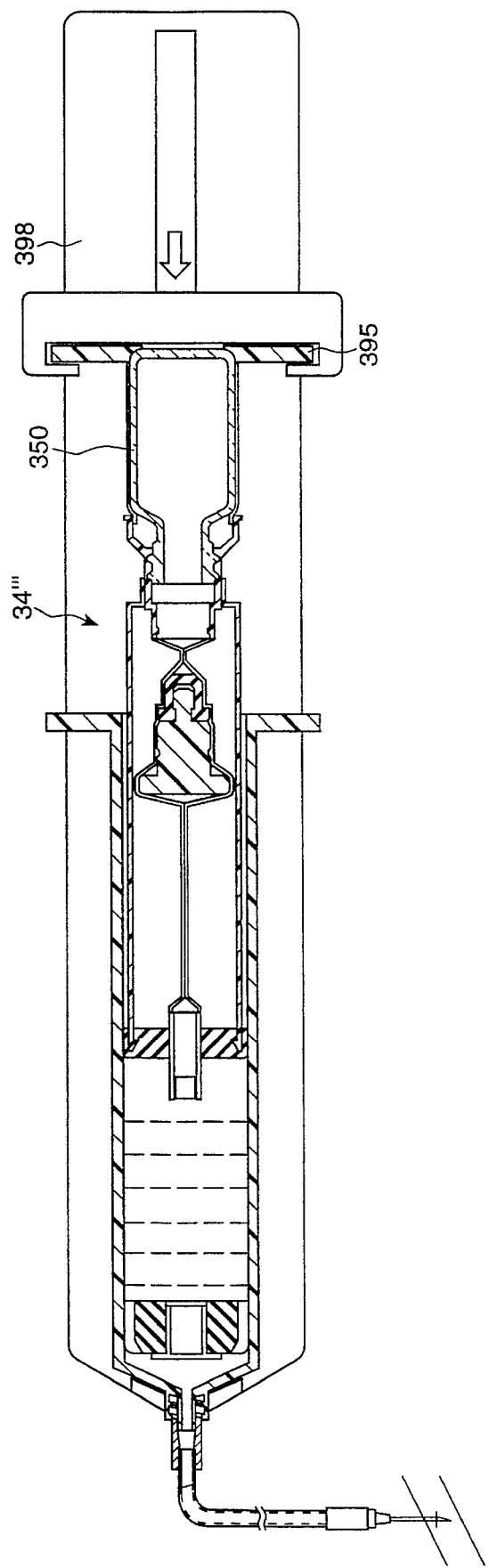
FIG. 15G is a partial cross-section view according to the embodiment of FIG. 15D, engaging a syringe pump and connecting to a catheter.

As shown in FIG. 15D, a flange 395 may be provided adjacent the drug vial 350 to allow the drug vial 350 and handle 34''' to be more easily retracted and advanced. The flange 395 can be sized to be received within an automatic, mechanical, or electronic syringe pump 398 (FIG. 15G). Furthermore, as shown in FIG. 15D, the drug vial 350 can be sized to be slidably received within the syringe barrel 10''' for more conventional operation and ease of interface with conventional syringe pumps. If preferred, for interfacing with syringe pumps, a neck (not shown) having the configuration of a conventional syringe handle can be provided intermediate the flange 395 and adjacent the drug vial 350 to facilitate operation with conventional syringe pump designs.

In operation, drug vial 50''' with the attached sealing plug 330 is threadably engaged with the drug vial retainer 324 so that plug 330 is tightly retained about reservoir plug 360 (FIG. 15E) prior to complete insertion into barrel 10''' of handle 34'''. The user can then contact plug rim 364 through windows 366 and advance plug 360 distally so that the reservoir plug 360 and the retained vial plug 330 are displaced away from vial opening 60''' Diluent from reservoir 370 can then freely flow into drug vial chamber 51 ''' through opening 60''' to mix the drug formerly retained within the vial 50''' and the diluent formerly retained within the reservoir 350. Free flow of diluent and mixed solution can be achieved through the large vial opening 60'''. The syringe 5''' can be rocked and rolled so as to provide complete mixing. Once mixing is complete, handle 34''' can be grasped and retracted. Retraction of handle 34''' will cause proximal piston 70''' to be displaced away from the retained distal stopper 74''' so that cap 390 is disengaged from tube 374.

In addition, negative pressure within bore 22''' will develop since conduit 26''' is sealed by cap 19. This will open one-way valve 384 to cause the mixed drug solution contained within the reservoir 350 and vial 50 ''' to flow into the syringe barrel bore 22''' through the now opened lumen 378. Once all of the fluid has been displaced into the barrel 22''', further retraction of handle 34''' is inhibited by the development of negative pressure within the barrel 22''' distal to piston 70''' The retraction maneuver is preferably performed with the syringe 5''' in a position wherein the distal tip 18''' is directed downward to assist in the free flow of fluid out lumen 378 and into contact with inner barrel wall 12'''. Upon complete withdrawal of handle 34''' (FIG. 15F), flexible reservoir 350 has collapsed, effectively reducing the transmission of negative pressure from within the syringe barrel 22''' to within the drug vial 50''', although such transmission of negative pressure is not seen as detrimental with the presently preferred embodiment. After the mixed drug solution has been drawn within bore 22''' into contact with the barrel wall 12''' distal the retracted proximal piston 70''', the drag solution is ready for injection. Distal tip cap 19 can then be removed and conduit 26''' placed in fluid connection with the intended recipient of the drug solution for subsequent injection of the drug solution. The drug solution is injected by advancing handle 34''', thereby advancing proximal piston 70'''. During advancement, positive pressure within bore 22''' distal the proximal piston 70''' causes the one-way 384 to close so that drug solution does not reflux through lumen 378 back into reservoir 350. A potential to reduce development costs by interfacing with a variety of conventional drug vial systems provides a substantial value to this present embodiment.

A further embodiment (shown in FIG. 18A), functions in a manner similar to the embodiment of FIG. 6, but having the advantage of providing for positive displacement of a proximal piston along an inner drug vial wall to displace the drug from the drug vial, as will be discussed. This embodiment, (numbered similar to FIG. 6, but with 600s) utilizes a vial piston assembly 638 including a cylindrical drug vial 650 which is open at a distal end 660 and a proximal end 661. A distal piston 674 having circumferential flow channels or slots 678 is sealingly received into the distal end 660 of vial 650. The proximal piston 670 is sealingly received into the proximal end 661. A barrel 610 is provided with a bore 622, having an inner wall 612 for receiving a slideable rubber, circumferential, sealing wiper 654 surrounding the drug vial 650. A handle 634 is provided, having distal retainers 636 for retaining the handle 634 within the circumferential wiper 654. A stop-rod 680 is provided, having a pair of proximal stops 682 and a threaded distal end 684. The threaded end 684 is sized to be threadably received within proximal stopper 670. The stop-rod slides within opposing slots 685 and 686 along handle 634. The length of slots 685 and 686 is equal to the relative displacement length of the proximal piston 670 along drug vial 650, as will be described. The stops 682 are sized to engage a proximal detent 688 along barrel 610 upon retraction of handle 634. The operation of this embodiment is quite similar to the embodiment of FIG. 6, except that this syringe 605 provides positive displacement of the contents of drug vial 650 into the mixing chamber 690 upon retraction of handle 634, as will be discussed.

In initial assembly, the handle 634 and attached vial piston assembly 638 is loaded into the syringe barrel 610 and fully advanced to the distal tapered end 614. As previously discussed for earlier embodiments, the distal stopper 674 has a greater diameter than the syringe barrel bore 622 so that the distal stopper 674 is compressed by the syringe barrel 610 to provide tight frictional engagement in the maximally advanced position of FIG. 18A. Withdrawal of handle 634, as in FIG. 18B, causes drug vial 650 to be displaced away from distal stopper 674 to widely open the drug vial chamber 651 into a nascent mixing chamber 690. In addition, retraction of handle 634 causes negative pressure to develop in chamber 690 and thereby causes fluid to flow through conduit 626 and through slots 678 into mixing chamber 690. During the retraction of handle 634 and the attached drug vial 650, the stop-rod 680 is slidably displaced along slots 685 and 686. As shown in FIG. 18D, further retraction of handle 634 and the attached vial 650 causes stops 682 to engage annular detent 688, thereby causing positive relative advancement of stop-rod 680 and the attached piston 670 along drug vial wall 652 and past drug vial detent: 694 so that the proximal piston 670 is retained adjacent the distal end 660 of drug vial 650. Once handle 634 has been fully retracted and stop-rod 680 and attached proximal piston 670 has been fully advanced along drug vial wall 652, substantially all of the drug formerly contained within drug vial chamber 651 has been positively expressed into nascent mixing chamber 690. The syringe 605 can then be agitated to facilitate mixing.

When injection is desired, the distal conduit 626 through distal tip 618 can be placed in fluid connection with the intended recipient. The handle 634 is then advanced. The proximal piston 670 and the stop-rod 680 are prevented from proximal displacement by retainer 694. Alternatively, complementing detents (now shown) could be provided along the slots 685 and 686 and stop-rod 680 to prevent displacement of the proximal piston 670 once the proximal piston 670 has been advanced along the vial 650, thereby eliminating the need for the vial retainers 694. During advancement, the drug solution contained within mixing chamber 690 is pushed through slots 678, out conduit 626, and into the intended recipient. It can be seen that the operation of this embodiment allows positive displacement of substantially all drug out of a drug vial 650 and into a mixing chamber 690 within a syringe 605 with a single handle 634 retraction maneuver. The embodiment further does not require the use of a tether, as described for some of the previous embodiments. This embodiment, therefore, has the advantage of simplified operation and manufacture. Markers or detents (not shown) can be provided along the handle 634 and the syringe barrel 610 for indicating that complete withdrawal and locking of the proximal piston 670 in the fully advanced position of FIG. 18D has been achieved.

Although the presently preferred embodiments of this invention have been described, it will be obvious to those skilled in the art that various changes and modifications may be made therein without departing from the invention. Therefore, the claims are intended to include all such changes and modifications which may be made therein without departing from the invention. Therefore, the claims are intended to include all such changes and modifications that fall within the true spirit and scope of the invention.

I claim:

1. A drug-mixing syringe comprising:

a. a barrel and a main bore, the barrel having a distal end and an opening through said distal end in fluid connection with said bore;

b. a drug vial having a longitudinal axis and distal end having an opening therein defined by an outer wall adjacent said end, said drug vial being sized to be slidingly received within said barrel;

c. a stopper having a distal face and a proximal face and being sized to be received within the open distal end of said drug vial and to occlude said distal end, said stopper defining an axis and including a distal portion having at least one member projecting beyond at least a portion of said outer wall of said drug vial and into engagement with an inner wall of said barrel bore when said drug vial and said stopper are inserted into said barrel bore, said at least one member being selectively displaceable relative to said barrel bore so that when said vial is inserted along said barrel bore, said at least one member is displaced along said barrel bore, and so that after said vial has been advanced to a particular extent, then retraction of said vial relative to said barrel bore causes said stopper to be displaced out of said distal end of said drug vial and retained in said barrel bore, said stopper defining at least one flow channel extending adjacent said distal portion when said stopper is received into said barrel so that when fluid flows through said barrel, fluid can flow through said flow channel.

2. The drug-mixing syringe of claim 1 wherein said distal portion has a transverse width greater than the width of the drug vial and wherein said flow channel extends through said stopper.

3. The drug-mixing syringe of claim 1 wherein said flow channel is free from communication with said drug vial chamber when said stopper is sealingly received into said drug vial.

4. A drug-mixing syringe comprising:
   a. a barrel having an inner wall and a main bore, the barrel having a distal end and an opening through said distal end in fluid connection with said bore;
   b. a reservoir sized to be received within said bore;
   c. a distal stopper carried by said reservoir and occluding said reservoir, at least a portion of said distal stopper engaging said barrel wall to retain said distal stopper in a fixed position along said bore after said reservoir and stopper have been advanced into said bore, so that after said reservoir has been so advanced and when said reservoir is subsequently retracted along said bore, said stopper is displaced away from sealing engagement with said reservoir to define an opening in said reservoir and to open said reservoir within said barrel so that fluid may flow within said barrel from said reservoir through said opening.

5. The drug-mixing syringe of claim 4 wherein said stopper includes at least one projecting member for engaging said barrel wall.

6. The drug-mixing syringe of claim 4 wherein said stopper defines at least one flow channel when said stopper is received into said barrel.

7. The drug-mixing syringe of claim 4 further including a piston assembly, the assembly including said distal stopper and a proximal piston and a connecting element intermediate said stopper and said piston.

8. The drug-mixing syringe of claim 4 wherein a cap is provided in sealing engagement with said reservoir and wherein said stopper is connected to said cap so that when said reservoir is displaced away from said stopper, said cap is displaced from sealing engagement with said reservoir to open said reservoir within said barrel.

9. The drug-mixing syringe of claim 4 further including a handle connected to said reservoir, said handle carrying said reservoir.

10. The drug-mixing syringe of claim 7 wherein said connecting element is a conduit in fluid connection with said reservoir and including a one-way valve along said conduit, said valve being responsive to a difference in pressure across said valve, said valve opening when the pressure within the barrel is less than the pressure within the reservoir, said valve closing when the pressure within the barrel is greater than the pressure within the reservoir.

11. The drug-mixing syringe of claim 9 wherein said handle is connected to said proximal piston and wherein said proximal piston is sealingly engaged with said barrel such that, when said handle is retracted and said proximal piston is retracted along said barrel, the pressure is reduced within said barrel relative the pressure within said reservoir so that fluid is displaced along the pressure gradient out said reservoir and into said barrel distal to said proximal piston.

12. The drug-mixing syringe of claim 9 further including a drug vial receiver carried by said handle for connecting said drug vial with said reservoir.

13. A drug-mixing syringe comprising:
   a. a barrel and a main bore, the barrel having a distal end and an opening through said distal end in fluid communication with said bore;
   b. a drug vial having an open distal end and a proximal end;
   c. a stopper occluding said distal end of said drug vial;
   d. said drug vial being sized to be received within said barrel and to be advanced along said barrel to an advanced position adjacent said distal end of said barrel, said stopper being sized to engage said barrel and to be retained by said barrel adjacent said distal end of said barrel, said stopper in said advanced position being fixedly engaged with said barrel adjacent said distal end so that after said vial and said stopper have been advanced within said barrel to said advanced position, said vial is displaced away from said retained stopper when said vial is retracted along said barrel to open said vial within said barrel.

14. The drug mixing syringe of claim 13 wherein said stopper includes at least one flow channel.

15. The drug mixing syringe of claim 13 further including a proximal piston adjacent said proximal end of said drug vial, said proximal piston being moveable along said vial to an advanced position within said vial adjacent said distal opening of said vial, said movement effectively displacing substantially all drug from within said vial into said barrel.

16. The drug mixing syringe of claim 15 further including a handle connected to said proximal piston, said handle functioning to advance said proximal piston along said vial, said handle further functioning to retract said vial away from said stopper when said stopper is retained by said barrel.

17. The drug mixing syringe of claim 13 wherein said stopper is connected to said proximal piston by a tensile element.

18. The drug mixing syringe of claim 17 wherein said tensile element is a tether.

19. The drug mixing syringe of claim 18 further including a vent extending through said tether.

20. A medical mixing syringe for mixing a diluent with a beneficial agent, the syringe comprising:
   a. a barrel having a main bore and further having an open proximal end and a distal end;
   b. a lumen extending through said distal end in communication with said main bore;
   c. a handle having a distal end and a proximal end and a portion intermediate said handle ends;
   d. a reservoir adjacent said intermediate portion, said reservoir defining a chamber for containing a pharmaceutical, said reservoir having a distal open end and a proximal end, said reservoir being sized to be received into said barrel and being moveable to an advanced position along said barrel;
   e. a piston sized to be received within said barrel, said piston being connected to said handle;
   f. a stopper connected about said distal open end of said reservoir and occluding said distal reservoir end, said stopper including a member for engaging said barrel, said stopper being sized to be received within said barrel, said stopper being moveable with said reservoir to an advanced position along said barrel, said stopper member engaging said barrel to prevent retraction of said stopper from said advanced position and to retain said stopper in said advanced position within said barrel so that when said reservoir is retracted from said advanced position said reservoir is displaced away from said stopper to open said reservoir into said barrel so that [fluid may flow]said pharmaceutical may pass from out of said reservoir and into said barrel.

21. The mixing syringe of claim 20 wherein said reservoir is a flexible polymeric container.

22. The mixing syringe of claim 21 wherein said reservoir is collapsible.

23. The mixing syringe of claim 22 wherein said reservoir is comprised of polyvinyl chloride.

24. The mixing syringe of claim 20 further including a drug vial connector adjacent said proximal reservoir end.

25. The mixing syringe of claim 20 wherein said stopper and said piston are connected by a connecting element.

26. The mixing syringe of claim 25 wherein said connecting element is a tube in fluid communication with said reservoir.

27. The mixing syringe of claim 20 wherein said stopper defines, in said advanced position, at least one flow channel so that liquid within said barrel can be injected past said stopper through said channel.

28. The mixing syringe of claim 20 wherein said advanced position is adjacent said distal end of said barrel.

29. The syringe of claim 20 wherein said barrel defines an axis and a main bore having a transverse dimension at said advanced position and wherein said stopper defines an axis, said stopper and having at least a portion being elastically compressible, the portion having a transverse dimension exceeding said transverse dimension of said bore so that when said stopper is advanced into said bore, said portion is compressed against said bore to retain said stopper within said bore.

30. The syringe of claim 20 wherein said barrel includes a retaining member for engaging and retaining said stopper in said advanced position.

31. A syringe for mixing pharmaceutical agent with a diluent, the syringe comprising:
   a. a barrel and a main bore, the barrel having a distal end and an opening through said distal end in fluid connection with said bore;
   b. a drug vial defining an axis and having an open distal end and a outer wall adjacent said end, said vial being sized to be received within said barrel;
   c. a stopper having a distal face and a proximal face and being sized to be received within the distal end of said drug vial and to occlude said distal end, said stopper defining an axis and including a distal portion having a member for engaging said barrel, said member projecting beyond at least a portion of said outer wall of said drug vial when said stopper is sealingly received into said drug vial and when said drug vial and said stopper are inserted into said barrel bore;
   d. a handle connected to said drug vial for advancing and retracting said drug vial along said barrel;
   e. a sealing member mounted adjacent one said drug vial and said handle, the sealing member being sized to seal about said bore so that when said drug vial is advanced along said barrel, said sealing member seals circumferentially against said bore so that when said vial is so advanced, the pressure is increased within said bore distal to said vial and when said vial is retracted along said barrel, the pressure is decreased within said bore distal to said vial.

32. A system for storage and the enclosed sterile assembly of a syringe containing a pharmaceutical agent, the system comprising:
   a. a barrel and a main bore, the barrel having an open proximal end and a distal end and an opening through said distal end in fluid connection with said bore;
   b. a drug vial defining an axis and having an open distal end and a outer wall adjacent said end, said vial being sized to be received within said barrel;
   c. a stopper having a distal face and a proximal face and being sized to be received within the distal end of said drug vial and to occlude said distal end, said stopper defining an axis and including; a distal portion having a member for engaging said barrel, said member projecting beyond at least a portion of said outer wall of said drug vial when said stopper is sealingly received into said drug vial and when said drug vial and said stopper are inserted into said barrel bore;
   d. a handle connected to said drug vial for advancing and retracting said drug vial along said barrel;
   e. a flexible envelope enclosing said barrel, said handle, and said vial within a sealed sterile environment within said envelope, said envelope being sized so that said vial and said handle can be aligned with said open proximal end, and so that said vial can be sterilely inserted into said barrel within said envelope by contacting said handle and said vial through said envelope and manipulating said vial and said handle within said envelope.

33. The system of claim 32 further including a first syringe compartment for containing said barrel, said handle, and said vial and a second liquid compartment for enclosing a liquid for enclosed aspiration into said barrel, said syringe compartment and said liquid compartment being free from exposure to the environment outside said envelope when said liquid is aspirated into said barrel.

34. A method for the enclosed and sterile mixing of a pharmaceutical agent from a closed and sealed pharmaceutical vial with a diluent and for subsequent injection of the mixture into a patient using a syringe having a barrel, the vial having an open distal end sealed by a stopper, and having a proximal end and a piston adjacent said proximal end, the method comprising steps of:
   a. inserting the closed pharmaceutical storage vial into the barrel;
   b. advancing the pharmaceutical storage vial along the barrel;
   c. disengaging the stopper from sealing contact with the open end of the pharmaceutical vial;
   d. aspirating diluent into the main bore into contact with said pharmaceutical agent to derive a mixture of said diluent and said pharmaceutical agent;
   e. advancing said proximal piston along said vial, said piston expelling the pharmaceutical agent from the vial;
   f. advancing said vial to inject said mixture into a patient. a portion of said outer wall.

35. A drug-mixing syringe comprising:
   a. a barrel and a main bore, the barrel having a distal end and an opening through said distal end in fluid connection with said bore;
   b. a drug vial defining an axis and having an open distal end and a outer wall adjacent said end, said vial being sized to be received within said barrel;
   c. a stopper connected about said distal open end of said vial and occluding said distal vial end, said stopper including a member for engaging said barrel, said stopper being sized to be received within said barrel, said stopper being moveable with said vial to an advanced position along said barrel, said stopper member engaging said barrel to prevent retraction of said stopper from said advanced position and to retain said stopper in said advanced position within said barrel so that when said vial is retracted from said advanced position said vial is displaced away from said stopper to open said vial into said barrel so that fluid may flow from out of said vial and into said barrel.

36. The syringe of claim 35 wherein said stopper defines an axis and further includes a distal portion for engaging said barrel.

37. The syringe of claim 35 wherein said barrel engaging member projects beyond at least a portion of said outer wall.

38. The syringe of claim 35 wherein said stopper in said advanced position defines at least one flow channel so that when said stopper is retained in said advanced position, and when liquid flows through said barrel, liquid can flow through said flow channel.

39. The syringe of claim 38 wherein said flow channel extends through said stopper.

40. The syringe of claim 38 wherein said stopper forms a first wall of said flow channel and wherein said barrel forms a second wall of said flow channel.

41. The syringe of claim 37 wherein said portion has a transverse dimension greater than the transverse dimension of the drug vial so that said portion projects transversely beyond said vial wall.

42. The syringe of claim 35 wherein said vial has an open proximal end occluded by a piston.

43. The syringe of claim 42 wherein said piston is connected to a handle for advancing said piston along said vial and for advancing said vial along said barrel.

44. The syringe of claim 35 wherein said vial is connected to a handle for advancing and retracting said vial along said barrel.

45. The syringe of claim 35 further including a sealing member mounted adjacent one said drug vial and said handle, the sealing member being sized to seal about said bore so that when said drug vial is advanced along said barrel, said sealing member seals circumferentially against said bore so that when said vial is so advanced, the pressure is increased within said bore distal to said vial and when said vial is retracted along said barrel, the pressure is decreased within said bore distal to said vial.

46. A method for the enclosed and sterile mixing of a pharmaceutical agent from a closed pharmaceutical vial having an open end occluded by a stopper with a diluent, and for subsequent injection of the mixture into a patient using a syringe having a barrel, the method comprising steps of:
   a. inserting the occluded pharmaceutical storage vial into the barrel;
   b. advancing the pharmaceutical storage vial along the barrel;
   c. after the step of advancing, retracting said vial along said barrel;
   d. disengaging the stopper within said barrel from sealing contact with the open end of the pharmaceutical vial;
   e. aspirating said diluent into contact with said pharmaceutical agent;
   f. advancing said vial along said barrel to inject said mixture into a patient.

47. The method of claim 46 further including steps of disposing a flow channel through said stopper and injecting said mixture through said flow channel during the stop of advancing said vial along said barrel to inject said mixture.

48. The method of claim 46 further including steps of aspirating diluent through said flow channel during the step of retracting said vial along said barrel.

49. The method of claim 46 wherein said stopper is moveable along said barrel with said vial to an advanced position, said stopper including a member for engaging said barrel in said advanced position to retain said stopper in said advanced position, the method including the further step of retaining said stopper in said advanced position during the step of retracting said vial along said barrel.

* * * * *